US 6,605,666 B1

United States Patent
Scholz et al.

(10) Patent No.: US 6,605,666 B1
(45) Date of Patent: *Aug. 12, 2003

(54) POLYURETHANE FILM-FORMING DISPERSIONS IN ALCOHOL-WATER SYSTEM

(75) Inventors: Matthew T. Scholz, Woodbury, MN (US); Steven S. Kantner, St. Paul, MN (US); Kristen L. Comstock, St. Paul, MN (US); Christopher J. Brown, New Brighton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/627,110

(22) Filed: Jul. 27, 2000

(51) Int. Cl.$^7$ .............................. C08J 3/03; C08J 3/09; C08G 18/28; A61B 19/08

(52) U.S. Cl. ...................... 524/591; 128/849; 128/850; 424/78.02; 424/78.03; 424/78.37; 427/2.1; 524/839; 524/840; 528/71

(58) Field of Search .................. 524/591, 839, 524/840; 528/71; 424/78.02, 78.03, 78.37; 427/2.1; 128/849, 850

(56) References Cited

U.S. PATENT DOCUMENTS

| | | | |
|---|---|---|---|
| 3,479,310 A | 11/1969 | Dieterich et al. | 524/591 |
| 3,600,359 A | 8/1971 | Miranda | 558/240 |
| 3,700,643 A | 10/1972 | Smith et al. | 526/282 |
| 4,307,219 A * | 12/1981 | Larson | 528/71 |
| 4,507,430 A * | 3/1985 | Shimada et al. | 524/839 |
| 4,542,012 A | 9/1985 | Dell | 424/28 |
| 4,558,149 A | 12/1985 | Larson | 560/14 |
| 4,667,661 A | 5/1987 | Scholz et al. | 128/90 |
| 4,978,527 A | 12/1990 | Brink et al. | 424/78 |
| 5,045,601 A * | 9/1991 | Capelli et al. | 528/112 |
| 5,173,291 A | 12/1992 | Brink et al. | 424/78.06 |
| 5,180,061 A | 1/1993 | Khan et al. | 206/570 |
| 5,302,385 A | 4/1994 | Khan et al. | 424/486 |
| 5,326,815 A * | 7/1994 | Serdiuk et al. | 524/591 |
| 5,334,650 A * | 8/1994 | Serdiuk et al. | 524/591 |
| 5,672,653 A | 9/1997 | Frisch et al. | 524/591 |
| 5,679,754 A | 10/1997 | Larson et al. | 528/28 |
| 5,855,208 A | 1/1999 | Askill et al. | 128/849 |
| 5,951,993 A | 9/1999 | Scholz et al. | 424/405 |
| 6,433,073 B1 * | 8/2002 | Kantner et al. | 524/591 |

FOREIGN PATENT DOCUMENTS

| | | |
|---|---|---|
| EP | 0 039 162 | 11/1981 |
| EP | 0 299 148 | 1/1989 |
| EP | 0 807 647 | 11/1997 |
| WO | WO 99/48941 | 9/1999 |

OTHER PUBLICATIONS

C. R. Noller, *Chemistry of Organic Compounds*, Ch. 6, pp. 121–122 (1957).

* cited by examiner

*Primary Examiner*—Rabon Sergent
(74) *Attorney, Agent, or Firm*—Nancy M. Lambert

(57) ABSTRACT

A polyurethane dispersion and method of making are provided. The dispersion is stable in an alcohol-water mixture. The dispersion is a reaction product of: (i) at least one oligomeric polyactive hydrogen compound, wherein said compound is an alkyl, aryl, or aralkyl structure optionally substituted in and/or on the chain by N, O, S and combinations thereof, and wherein the compound is insoluble in 50:50 weight percent of said alcohol-water mixture; (ii) at least one polyisocyanate, and (iii) at least one polyactive hydrogen compound soluble in the alcohol-water mixture selected from the group consisting of a compound containing an ionic group, a compound containing a moiety capable of forming an ionic group, a compound containing a polyester, polyether, or polycarbonate group having a ratio of 5 or less carbon atoms for each oxygen atom, and mixtures thereof; and (b) at least one polyfunctional chain extender.

29 Claims, 1 Drawing Sheet

POLYURETHANE FILM-FORMING DISPERSIONS IN ALCOHOL-WATER SYSTEM

TECHNICAL FIELD

The present invention pertains to a composition in the form of a stable hydroalcoholic polyurethane dispersion containing polymers. The composition exhibits film-forming properties and can be formulated to have anti-microbial activity.

BACKGROUND

Polyurethane is a generic term used to describe polymers prepared by the reaction of a polyfunctional isocyanate with a polyfunctional alcohol to form urethane linkages. The term "polyurethane" has also been used more generically to refer to the reaction products of polyisocyanates with any poly-active hydrogen compound including polyfunctional alcohols, amines, and mercaptans. Polyurethanes are used in a variety of applications including as elastomers, adhesives, coatings, and impregnating agents.

For coating applications, polyurethane polymers can be dispersed in water by incorporating stabilizing groups into their backbone. Anionic, cationic and non-ionic dispersion stabilizing groups have been used. Various aqueous polyurethane dispersions have been prepared by those skilled in the art. For example, U.S. Pat. No. 3,479,310 (Dieterich et al.) discloses water-dispersed polyurethane polymers suitable for uses as waterproof coatings. The polymer is prepared from polyhydroxy compounds, polyisocyanates, optional chain lengthening agents, and a sufficient amount of a component having an ionic salt-type group. U.S. Pat. No. 4,307,219 (Larson) discloses dispersible polyurethane resin prepared by reaction of hydrophilic diols, hydrophobic diols, diisocyanates, and, optionally, chain extenders. Such a urethane resin can be used as protective coatings, primers, and binders.

Although aqueous dispersions of polyurethanes have been widely disclosed, the inventors are not aware of any references to stable polyurethane dispersions in alcohol-water solvent systems, particularly when prepared from very hydrophobic polyols. Polyurethane dispersions in hydro-alcohol (i.e., alcohol-water) systems are especially difficult for at least two reasons.

First, the addition of lower alcohols (e.g., $C_1$ to $C_4$) to water decreases the surface tension of the solvent system. For example, a 40 weight percent (wt %) ethanol in water system has a surface tension of about 31 dyne/cm compared to a pure water system, which has a surface tension of about 72 dyne/cm at about 20° C. A 60 wt % ethanol in water system has a surface tension of 27 dyne/cm at about 20° C. The reduction in surface tension can affect the ability to self assemble hydrophilic and hydrophobic domains during the dispersion preparation. Second, many of the polyurethane components (i.e., the starting reactants) are soluble in hydro-alcohol solvent systems, which result in solutions and not dispersions. Polymer solutions have substantially higher viscosity than polymer dispersions, making them harder to process in certain operations, such as coating and spraying operations. Polymer solutions also tend to achieve lower percent solids when compared to polymer dispersions, making the former less attractive during coating operations and during shipping. Lower solids solutions also require longer drying times than dispersions to form a film because of the greater amount of solvent present the higher affinity of the polymer for that solvent, and the immediate formation of a "skin" on the surface of the film as it begins to dry. Furthermore, the molecular weight of soluble polymers is often much lower than that of dispersions.

U.S. Pat. No. 4,507,430 (Shimada et al.) discloses a water-based polyurethane emulsion that comprises a hydrogenated polyalkadiene polyol component and a polyisocyanate component. Shimada discloses that the materials are useful as an adhesive or coating material for a polyolefin resin, and can be applied wet and dried or bonded by dry lamination requiring heat and pressure. While the hydrogenated polyalkadiene polyol component of Shimada is alcohol-water insoluble, there was no disclosure of polyurethane dispersions in hydro-alcohol solvent system.

U.S. Pat. No. 5,672,653 (Frisch et al.) discloses an anionic waterborne polyurethane dispersion prepared by (a) forming a prepolymer from hydroxy terminated polybutadiene resin, an aliphatic isocyanate, and a diol containing acid groups; (b) neutralizing the acid; dispersing it in water; and (c) chain extending the prepolymer with a diamine.

U.S. Pat. No. 4,542,012 (Dell) discloses a dermatologically acceptable film-forming composition. The composition comprises (a) a film-forming polymer that is a reaction product of (i) a prepolymer having a plurality of isocyanate functionalities, (ii) a polyvinyl pyrrolidone polymer; and (iii) a chain extender for the prepolymer and the polyvinyl pyrrolidone polymer; and (b) as an anti-microbial agent, iodine, which forms a complex with the film-forming polymer. The polymer so formed is soluble in the hydroalcoholic solvent. The composition, when applied to skin from a fugitive solvent, is capable of forming a substantially water insoluble, tack-free, flexible film that adheres to skin, releases the anti-microbial agent when the film contacts skin. The film exhibits an elongation of at least about 150% and less than about 1000%.

A need exists in the art for polyurethane dispersions that exhibit anti-microbial activity and are stable in alcohol-water solvent systems, where the dispersion has one or more of the following properties: capable of forming stable dispersions in hydro-alcohol systems, capable of rapidly forming films on skin by simple ambient evaporation, and are compatible with antimicrobial agents. Furthermore, films formed by drying down the dispersions exhibit one or more of the following properties: high self adhesion and yet low tack, low humidity sensitivity, high tensile strength, good elongation, transparent, and capable of releasing added antimicrobial agents.

SUMMARY

The present invention provides a novel polyurethane-urea dispersion that can be prepared in the presence of and is dispersed in a hydro-alcohol system. As used herein, the term "hydro-alcohol" refers to solvents based on $C_1$ to $C_4$ lower alcohols mixed with water, where the weight ratio of lower alcohol to water is at least 20:80, preferably at least 40:60, more preferably at least 50:50 and most preferably at least 60:40 by weight. It has been found that rapidly drying dispersions can be formed in hydro-alcohol solvent systems where the ratio of lower alcohol to water is at least 70:30, more preferably at least 80:20 and most preferably at least 85:15 by weight. The preferred lower alcohols include ethanol, 2-propanol, and n-propanol. The term "hydro-alcohol" is synonymous with the term "alcohol-water."

The polyurethane polymer exists as a dispersion in alcohol-water solvent system. As used herein, a "dispersion" means generally a two phase system where one phase contains discrete particles distributed throughout a bulk substance, the particles being the disperse or internal phase, and the bulk substance the continuous or external phase. In this invention, the continuous phase is the alcohol-water mixture and at least a portion of the polyurethane exists as the discrete particle. By "dispersion," it is also meant that not necessarily the entire polyurethane polymer needs to be alcohol-water insoluble; at least some of the polymer can be soluble in the alcohol-water mixture. In preferred rapid drying applications, most or all of the polymer is in the dispersed phase. Dispersions are possible through the use of certain components that are insoluble in the alcohol-water solvent system. It is desirable that the dispersion remain stable under ambient conditions. Preferred dispersions are stable at room temperature for more than 30 days, preferably more than 90 days, more preferably for more than 180 days, and most preferably for more than 360 days.

In brief summary, in one aspect, the invention provides a polyurethane dispersion stable in a lower alcohol-water mixture. The dispersion is a reaction product of (a) an isocyanate functional prepolymer comprising the reaction product of: (i) at least one polyactive hydrogen compound, wherein said compound is an alkyl, aryl, or aralkyl structure optionally substituted in and/or on the chain by N, O, S, and combinations thereof, and wherein the compound is insoluble in said lower alcohol-water mixture, when the alcohol to water ratio is at least 50:50 by weight (referred to as the "A" component for convenience); (ii) at least one polyisocyanate, and (iii) at least one active hydrogen compound soluble in the alcohol-water mixture, the compound selected from the group consisting of a compound containing an ionic group, a compound containing a moiety capable of forming an anionic group, a compound containing a polyester, polyether, or polycarbonate group having a ratio of 5 or less carbon atoms for each oxygen atom, and mixtures thereof (referred to as the "B" component for convenience); and (b) at least one polyfunctional chain extender, where the equivalent ratio of active hydrogen on the chain extender to isocyanate on the isocyanate functional prepolymer is 0.60:1 to 1.20:1.

In one embodiment, the dispersion further comprises anti-microbial agents. Such a dispersion can be used as a liquid drape functioning as a preoperative patient prep. When the dispersion dries to form a film, the film can function as an incise drape.

As used herein, a "liquid drape" means a dermatologically acceptable film-forming dispersion that can be applied (e.g., painted or sprayed) onto a patient's skin. The drape dries on the skin to form a film less than about 10 minutes, preferably less than about 5 minutes, and more preferably less than about 2 minutes upon application at temperatures of about 25° to 35° C., preferably about 29° to 32° C. The lower alcohol-water solvent system can function as an effective antimicrobial agent if the ratio of lower alcohol to water is about 60:40 to 90:10. In addition the liquid drape may contain an additional or secondary anti-microbial agent. Secondary antimicrobial agents are generally added to impart persistent antimicrobial activity. The drape preferably has properties, such as elongation of about 100% to 700% and tensile strength greater than about 2.5 lb/inch width for a 1 mil (0.025 mm) thick film. Such properties allow the drape to withstand the stresses imposed on it during certain processes, such as during an operation. For example, in some medical operations, it is common practice for a medical practitioner to apply a liquid drape on the patient at the operation site. After the liquid drape dries and forms a film, the practitioner may make an incision through the drape and the patient's skin. In some cases, the practitioner may need to widen the incision site. Under such circumstances, the drape should be able withstand the stresses imparted by the incision as well as the widening steps. The drape should also be adhered to the patient's skin during the entire operation. The drape preferably is not permeable to water or body fluids. In addition, in certain instances, it may be beneficial for the drape to have self adhesion.

As used herein, a material possesses "self adhesion" properties when it preferentially adheres to itself or a chemically similar material under pressure or force without the need for significantly elevated temperatures (e.g., without the need for temperatures above about 50° C.). Preferred compositions of the invention exhibit self adhesion properties immediately upon contact to itself at room temperature (about 20° to 30° C.). As used in the previous sentence, the term "immediately" means less than a few minutes, e.g., about 5 minutes, preferably less than 1 minute, more preferably less than 30 seconds, depending on the application. A potential benefit of high self adhesion formulations is the ability to coat the same or similar formulations on the underside (patient contact side) of additional patient covering drapes. These drapes can then be fixed in place by simply contacting and optionally pressing them against the dried self adherent incise drape. This can significantly facilitate the draping procedure. Thus, another aspect of the invention involves a kit or a system that contains a drape (or medical materials used on patients during surgery) that has at least a portion coated with the inventive dispersim. Optionally included in the kit is the inventive dispersim in the form of a liquid prep.

An advantage of the invention is the use of oligomeric polyactive hydrogen compounds that are insoluble in the alcohol-water solvent mixture when the ratio of lower alcohol to water is at least 50:50 by wt. Such a compound is typically hydrophobic and provides faster drying and improved hydrolytic stability over prior art liquid drapes. These hydrophobic polyols provide excellent adhesion to skin as well as imparting fluid resistance (such as resistance to water) to the dried film. A further advantage of the inventive dispersion is that it possesses a short cure time, as defined in the Example section. Both short dry time and short cure time are desirable properties in a liquid drape application.

Yet another advantage of the inventive dispersion is that it has low viscosity, high percent solids, able to form hydrophobic films, and is a dispersion. All these factors contribute to short dry time and short cure time, allowing the dispersion to form a film quickly once applied to the skin.

DETAILED DESCRIPTION OF THE INVENTION

Figure 1:
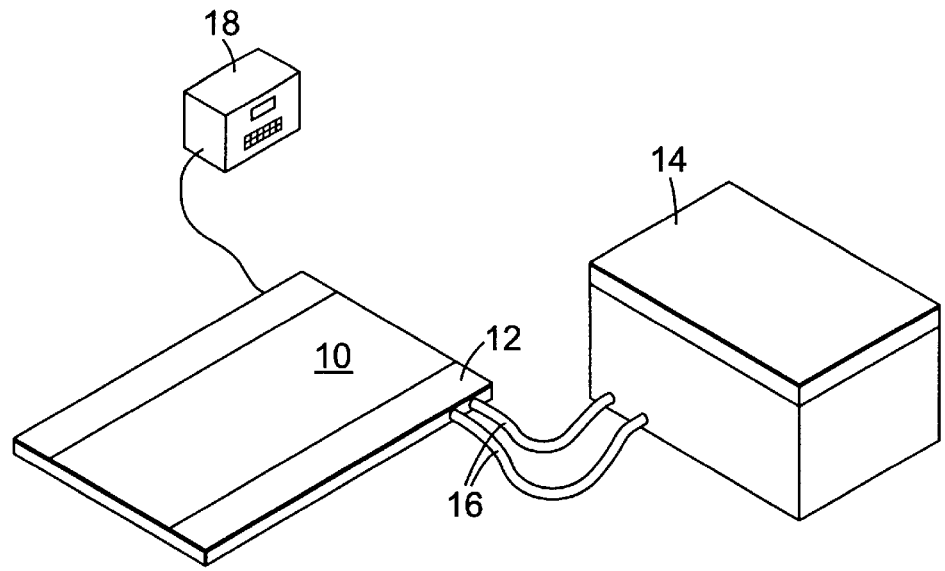
FIG. 1 is a schematic diagram of a means for measuring dry time and cure time of the present invention.

In brief summary, the inventive dispersion is made by forming the isocyanate functional prepolymer, chain extending the prepolymer, and optionally chain terminating the prepolymer to yield a polyurethane dispersion. Although it is presently preferred to carry out the foregoing steps sequentially, this is not necessary. The order of the steps may be changed and certain steps can be combined, such as chain extension and chain termination or prepolymer formation and chain termination, etc. The steps, and the components necessary to carry them out, are discussed in detail below.

In use, the inventive dispersion is typically coated onto a substrate, such as skin or a liner, dried and cured to form a film. In one embodiment, the film exhibits self adhesion properties. For use as a preoperative patient prep and incise drape, the films preferably have a tensile strength, for a 0.001 inch (0.025 mm) thick film of greater than about 2.5 lb/inch width, more preferably greater than about 3 lb/inch width, and most preferably, greater than about 4 lb/inch width. The most preferred films have a tensile strength for a 0.001 inch thick film of greater than about 5 lb/inch width. Conformability of the films used for preoperative patient prep is also an important property. The preferred films have good elongation and may even be elastomeric in nature. The film's elongation at break should be at least 100%, more preferably greater than 200%, and most preferably greater than 300%.

For an ionic dispersion, a solution containing polyion of the opposite charge can be applied to the film to create an instantaneous tack-free film. For example, an anionic dispersion can be coated and before it has formed a film, a solution containing polyvalent cation is sprayed on the coating's surface to yield a tack free film. This method is commonly referred to as "cospraying." A preferred solution contains water and metal cations, such as calcium and magnesium. Preferably, the film becomes tack free almost instantaneously after spraying the water solution (i.e., within a minute, preferably within a few seconds). In applications where very rapid tack-free times are required, such as in preoperative preparation for surgery, it may be beneficial to mist or otherwise wet the surface of the film. By "tack-free," it is generally meant that the misted film contains little or no adhesion to other substrates at ambient conditions, typically from about 20° to 30° C.

As used herein the term "isocyanate terminated prepolymer" (alternately referred to as "isocyanate functional prepolymer") means a reaction product of at least one polyisocyanate and at least one polyactive hydrogen compound (i.e., polyol). In general, the reaction occurs with a molar excess of isocyanate groups to produce an oligomer, which may have urethane, urea, or thiourethane functional groups. The prepolymer can be prepared at an equivalent ratio of isocyanate groups to active hydrogen reactive groups of greater than 1.6, preferably greater than 1.8, and most preferably about 2.0 or greater.

As used herein, a "polyol" includes compounds containing active hydrogen in accordance with the Zerevitanov test described by C. R. Noller, *Chemistry of Organic Compounds,* Chapter 6, pages 121–122 (1957). The term "polyol" further means a compound having an average functionality greater than 1, preferably greater than 1.8, and most preferably about 2.0 or greater but less than about 6, preferably less than about 4, and most preferably about 3 or less. It is understood to include compounds that have (i) alcohol groups on primary, secondary, and tertiary carbon atoms, (ii) primary and secondary amines, (iii) mercaptans, and (iv) mixtures of these functional groups. Accordingly, polyurethane polymers can contain urea linkages, for example, from the reaction of isocyanate functional polyurethanes with amines, these polymers more appropriately being called polyurethane-ureas. Polyols useful for preparing the prepolymer have a molecular weight of 62 to 10000, preferably 200 to 5000, and most preferably from 400 to 3000.

"A" Component

The "A" component is preferably present at concentrations of at least 5%, preferably at least 10%, and most preferably at least 15% by weight, based on the total prepolymer weight. The "A" component is insoluble in the lower alcohol-water solvent mixture where the lower alcohol to water ratio is at least 50:50 by weight. In the sentence, the term "insoluble" means generally that at least 1 gram of the compound is not soluble in about 4 grams of alcohol-water at about 25° C., when the alcohol to water ratio is at least 50:50 by weight. Certain polyols may require heating to melt to determine whether they are insoluble using this characterization method. The alcohol used in this characterization method should be the same alcohol used to prepare the dispersion.

The compounds useful as the "A" component have a number average molecular weight preferably above about 300, more preferably above about 400, and most preferably above about 500, but preferably below about 10000, more preferably below about 5000 and most preferably below about 3000.

Several different types of polyols are suitable for use as the "A" component. Monomeric polyols, such as the $C_{36}$ dimer fatty alcohol available as PRIPOL 2033 from Unichema North America, Chicago, Ill., USA, can be used. Oligomeric polyols that have, on average, from about 1.6 to about 4 hydroxyl or amino groups are preferred. One type of preferred oligomeric polyol is aliphatic polyester polyol based on diacids and/or diols that have greater than 10 carbon atoms and preferably greater than 20 carbon atoms. Commercially preferred polyester polyols are PRIPLAST 3191, 3192, 3196, 3197, 1906, and 1907 from Unichema North America, Chicago, Ill., USA, which are believed to be based on 36 carbon atom diacid and/or diol. Specific constituents used in preparation of these diols are believed to be: for PRIPLAST 3192—dimer acid, adipic acid, and 1, 6-hexane diol; for PRIPLAST 3193—dimer acid and ethylene glycol; for PRIPLAST 3194—dimer acid, adipic acid, and ethylene glycol; for PRIPLAST 3196—dimer acid and 1,6-hexane diol; for PRIPLAST 3197—dimer acid and dimer diol; for PRIPLAST 1906—isophthalic acid and dimer diol; and for PRIPLAST 1907—terephthalic acid and dimer diol. The term "dimer acid" is understood to be a $C_{36}$ diacid formed by dimerization of unsaturated $C_{18}$ fatty acids and "dimer diol" is a $C_{36}$ difunctional polyol formed by hydrogenation of the $C_{36}$ dimer acid.

Another preferred oligomeric polyol is hydroxy terminated polyalkadienes including polybutadienes and polyisoprenes. A commercially preferred hydroxy terminated polybutadiene is POLY bd resin from Elf Atochem North America, Philadelphia, Pa., USA.

Yet another preferred oligomeric polyol is hydrogenated polyalkadiene polyols including hydrogenated polyisoprene and hydrogenated polybutadiene having no less than about 19 wt % 1,2-butadiene addition. Commercially preferred hydrogenated polybutadiene diols include KRATON L2203 from Shell Chemical, Houston, Tex., USA and POLYTAIL resins from Mitsubishi Chemical, Tokyo, Japan. A preferred oligomeric polyamine is amine terminated butadiene polymers and butadiene-acrylonitrile copolymers. A commercially preferred amine terminated butadiene-acrylonitrile copolymer is HYCAR ATBN from B.F. Goodrich, Cleveland, Ohio, USA.

Silicone polyols or polyamines and perflouroalkyl functional polyols may also be used. When it is desired to form films with good self adhesion. These polyols preferably should not be present in greater than about 5 wt % of the polyurethane, as their low surface energy properties would be expected to detract from the desired adhesion characteristics based on the teachings of U.S. Pat. No. 5,679,754 (Larson et al).

In addition to polyols that are insoluble in the alcohol-water mixture containing at least 50:50 lower alcohol to water by weight, low molecular weight "monomeric" polyols may be used in the prepolymer formation. Examples of the monomeric polyols include ethylene glycol, propylene glycol, butylene glycol, hexamethylene glycol, diethylene glycol, 1,1,1-trimethylolpropane, pentaerythritol, aminoethanol, and the like. When used, preferably the amount of the monomeric polyols should be kept low (e.g. less than about 10% by weight) to minimize the viscosity of the prepolymer.

The amounts of the polyol and isocyanate used to form the prepolymer affects the physical and chemical properties of the final dispersion. Properties that can be varied include, but are not limited to, ductility, water uptake, tensile strength, modulus, abrasion resistance, minimum film-forming temperature, glass transition temperature, ultraviolet light resistance, resistance to hydrolysis, and color stability. In general, longer chain polyols tend to provide dispersions and films made therefrom that are more ductile and have lower $T_g$, higher elongation, and lower tensile strength. In contrast, shorter chain polyols tend to provide dispersions and films made therefrom that have high modulus, greater tensile strength, and higher $T_g$. Aliphatic polyols tend to provide materials with decreased water uptake whereas diols containing heteroatoms in the backbone (i.e., aromatic polyols) tend to have increased water uptake. The amount of water left in the film can affect its tensile and elongation properties. In order to provide resistance to hydrolysis, polyols should be selected that are hydrolytically stable, such as polyether (e.g. polyethylene glycols, polypropylene glycols, and polytetramethylene glycols) and polysiloxane polyols, and polyols based on polyolefin backbones. Polyester polyols may be used that are hydrolytically resistant such as those based on hydrophobic subunits (PRIPLAST polyols from Unichema), those based on isophthalic acid, as well as polycaprolactone polyols. Other polyols are hydrogenated polybutadiene polyols, fluorinated polyether polys, silicone polyols, and the so called "silicone copolyols," which are polysiloxanes having pendant polyether chains terminated with alcohols or alkyl groups.

Polyisocyanates

Representative polyisocyanates that can be used to form the isocyanate functional polyurethane include aliphatic and aromatic polyisocyanates. Suitable polyisocyanates are preferably aliphatic or cycloaliphatic isocyanates. The aromatic isocyanates are less preferred as they tend to discolor in ultraviolet light making them undesirable in outdoor applications. Particularly preferred diisocyanates include dicyclohexylmethane 4,4'-diisocyanate (commonly referred to as $H_{12}MDI$) and 3,5,5-trimethyl-1-isocyanato-3-isocyanatomethylcyclohexane (commonly referred to as isophorone diisocyanate, abbreviated as IPDI), both available from Bayer Corp., Pittsburgh, Pa., USA under the trade designations DESMODUR W and DESMODUR I, respectively. Other preferred diisocyanates include (i) tetramethylene diisocyanate, (ii) 1,3-bis(isocyanatomethyl) cyclohexane, (iii) 1,3-bis(1-isocyanato-1-methylethyl) benzene, (iv) diphenylmethane 4,4'-diisocyanate (commonly referred to as MDI), (v) 4,4',4"-triisocyanatotriphenylmethane, (vi) polymethylene polyphenylene polyisocyanate (commonly referred to as polymeric MDI), (vii) toluene diisocyanate (commonly referred to as TDI), (viii) hexamethylene diisocyanate (commonly referred to as HDI), (ix) dodecamethylene diisocyanate, and (x) m- and p-xylene diisocyanate.

Other useful polyisocyanates include those described in U.S. Pat. No. 3,700,643 (Smith et al.) and U.S. Pat. No. 3,600,359 (Miranda), which are incorporated herein by reference. Mixtures of polyisocyanates can also be used, such as ISONATE 2143L, available from Dow Chemical Co., Midland, Mich., USA.

"B" Component

The polyurethaneprepolymer is made alcohol-water dispersible by using a "B" component having at least one alcohol-water soluble active hydrogen compound. Preferably, it is a polyactive hydrogen compound. The B component acts primarily to stabilize the polyurethane dispersion in a water or alcohol-water solvent system. The phrase "alcohol-water soluble" means generally that at least 1 gram of the compound is soluble in about 4 grams of an alcohol-water mixture at about 25° C. Certain compounds may require heating to melt to determine whether they are soluble using this characterization method. In general, soluble polyols in a homogenous single phase appear visually transparent. The alcohol-water mixture used in this characterization method should be the same alcohol-water mixture used to prepare the dispersion. Alcohol-water solubility is imparted to the "B" component by the presence of an ionic group, a moiety capable of forming an ionic group, a non-ionic stabilizer in the form of poly($C_2$ to $C_4$) alkyl ether, and mixtures thereof. In general, as the concentration of the "A" component increases, the amount of stabilizer should also be increased to maintain a stable dispersion. When present, the ionic group of the "B" component can be anionic, cationic, or zwitterionic.

The cationic groups may originate from the isocyanate or polyol component but, most conveniently, are added in as a polyol component. Preferred stabilizing cationic components are very water soluble, generally have a solubility in water of at least 1 wt % and preferably in excess of 10 wt %. For example, N-alkyl dialkanolamine, a tertiary amine, may be added as a polyol, which reacts into the polymer backbone. The tertiary amine can be protonated or quaternized prior to or after the formation of the prepolymer to form the stabilizing cationic component. Preferred stabilizing cationic compounds have the following structure:

where

R is $C_1$ to $C_{18}$ alkyl or $C_6$ to $C_{18}$ aryl or aralkyl optionally substituted in available positions in or on the chain by N,O, and S;

$R_2$ is hydrogen or $C_1$ to $C_{18}$ alkyl;

n is an integer from about 1 to 200, preferably about 1 to 50, and most preferably about 1 to 20; and X is halogen, sulfate, methosulfate, ethosulfate, acetate, carbonate, or phosphate.

Preferred cationic stabilizing compounds include protonated and alkylated methyl diethanol amine as well as PEG 2 cocomonium chloride and PEG-15 cocomonium chloride available from Witco/Sherex as VARIQUAT 638 and VARIQUAT K1215 respectively. Examples of other suitable alcohol functional quaternary ammonium salts inlcude the following compounds, which can be found in the CTFA Cosmetic Ingredient Handbook, Second Ed., published by The Cosmetic, Toiletry, and Fragrance Association: Quaternium 52 (believed to be a polyethoxylated stearltriethanolamine, available from Henkel Corp., as DEHYQUART SP), Quaternium 80 (believed to be a polydimethylsiloxane terminated in alkyldimethylammonium-hydrodoxypropylpropylether groups, available from Goldschmidt Chemical Corp., Hopewell, Va. as ABIL QUAL 3270, 3272, and 3474), and Quaternium 82 (believed to be 1,1-dipropyloleate-2,2-dihydroxypropyl-2-methyl ethylenediamine methosulfate).

It is possible to incorporate stabilizing compounds that have a single reactive hydrogen group. However, they are less preferred. In the case of cationic polymers, the cationic group may be incorporated directly into the prepolymer. Alternatively, a precursor group can be reacted into the prepolymer and then be rendered cationic in a subsequent reaction. For example, a quaternary diol such as VARIQUAT K1215 may be reacted into the prepolymer directly. Alternatively, active hydrogen functional tertiary amines, such as methyldiethanolamine and its polyethoxylated adducts, may be incorporated into the prepolymer backbone and subsequently protonated with a mineral or organic acid to form an ionic salt or alkylated to form a quaternary ammonium group. Reaction of the incorporated tertiary amine with hydrogen peroxide, propane sultone or lactone gives zwitterionic moieties.

The anionic stabilizer used in the present invention can be present on either the isocyanate component or the polyol component. Typically, and most conveniently, the anionic stabilizer is present as the polyol component. The anionic group can be sulfonate, phosphonate, phosphate, and carboxylate but is preferably either sulfonate or carboxylate, and most preferably a sulfonate. The most preferred sulfonates are the sulfonated polyols (also referred to as "sulfopolyols") described in U.S. Pat. No. 4,558,149. Particularly preferred sulfonates are polyesterdiols having the following structure:

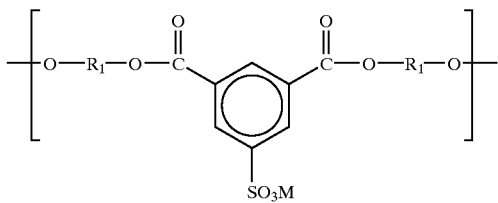

wherein each $R_1$ is independently a divalent aliphatic group having an average molecular weight of 200 to 2000, preferably 200–600 comprising ether or ester functional groups selected from the group consisting of poly ($C_2$ to $C_4$ alkylene oxide); preferably —$CH_2$—$CH_2$—($OCH_2$—$CH_2$—)$_n$—, —$C(CH_3)H$—$CH_2$—($OC(CH_3)H$—$CH_2$—)$_n$—, —$(CH_2)_4$—$(O(CH_4))_n$—;

and

—$(CH_2)_m$—CO—[—O—$(CH_2)_m$—CO—]$_n$— groups and mixtures thereof; where m is an integer from about 2 to 5 and n is an integer from about 2 to 15, and M is a cation, preferably M is Na, but M can be H, K, Li, or a primary, secondary, tertiary, or quaternary ammonium cation such as ammonium, methylammonium, butylammonium, diethylammonium, triethylammonium, tetraethylammonium, and benzyltrimethyl-ammonium cation.

Suitable carboxylic and carboxylate acid functional polyols include dimethylolpropionic acid and its polyethoxylated derivatives as well as acid grafted polyethers such as the UCARMOD polyols available from Union Carbide Specialty Chemicals Div., Danbury, Conn. These can be neutralized with an organic or inorganic base either before or after preparation of the prepolymer.

To obtain alcohol-water or water dispersibility, the ionic equivalent weight of the prepolymer (gram prepolymer per equivalent of ionic functionality) should be in the range of 1000 to 15000, preferably 1500 to 12500, more preferably 2000 to 10000, most preferably 2500 to 7500.

It has been found that poly (i.e., $C_2$ to $C_4$) alkyl ethers can function as non-ionic stabilizers. For example, ethylene oxide adduct moieties can be added as the sole stabilizer or in addition to the ionic groups in the polyurethane polymer chain. The ethylene oxide compounds can be any compound derived from the reaction of ethylene oxide having at least one active hydrogen group with the optional addition of other alkylene oxide comonomers in a random or block fashion. Preferred ethylene oxide compounds comprise at least two (2) active hydrogen groups. Examples of suitable ethylene oxide stabilizing compounds include homopolymers of polyethylene oxide (e.g., CARBOWAX), block copolymers of ethylene oxide and propylene oxide (e.g., PLURONIC from BASF Corp., Mount Olive, N.J.), random copolymers of ethylene oxide and propylene oxide (e.g., UCON FLUIDS, from Union Carbide, Danbury, Conn.), silicone copolyols, and surfactants based on polyethylene oxide as described in U.S. Pat. No. 4,667,661 (Scholz et al). Surprisingly, it has been found that other higher alkyl polyethers can function as non-ionic stabilizers in alcohol-water solvent systems. For example, polypropylene glycols and even poly(tetramethylene ether) can stabilize dispersions in hydro-alcohol systems, in which the alcohol to water ratio exceeds about 65:35. The effectiveness of this and other stabilizers is, of course, dependent on the chemical nature of the polyurethane being dispersed and the solvent system.

Examples of oligomeric polyols that have sufficient polar non-ionic groups such as ether or ester functionality to give alcohol-water solubility include (i) polyoxyalkylene diols, triols, and tetrols, (ii) polyoxyalkylene diamines and triamines, (iii) polyester diols, triols, and tetrols of organic polycarboxylic acids and polyhydric alcohols, and (iv) polylactone diols, triols, and tetrols having a molecular weight of 106 to about 2000. Preferred oligomeric polyols and polyamines include (i) polyethylene oxide homopolymers (e.g., CARBOWAX series from Union Carbide, Danbury, Conn.), block copolymers of ethylene oxide and propylene oxide (e.g., PLURONIC surfactants from BASF Corporation, Mount Olive, N.J.), random copolymers of ethylene oxide and propylene oxide (e.g., UCON FLUIDS from Union Carbide, Danbury, Conn.), silicone copolyols, as well as surfactants based on polyethylene oxide as described in U.S. Pat. No. 4,667,661 (Scholz et al.), (ii) polyoxypropylene diols and triols such as the ACCLAIM series of polyols from Arco Chemical, Newtown Square, Pa., (iii) polyether diamines and triamines such as the JEFFAMINE series available from Huntsman Corporation, Salt Lake City, Utah, (iv) polyether polyols such as the TERATHANE series (which is a polyoxytetramethylene diol) available from E.I. du Pont Co., Wilmington, Del., and the POLYMEG series available from Quaker Oats Co., Chicago, Ill., (v) polyester polyols such as MULTRON, which is a poly(ethyleneadipate)polyol, available from Bayer Corporation, Pittsburgh, Pa., (vi) polycarbonate diols such as those available from Stahl USA Co., Peabody, Mass., and (vii) polycaprolactone polyols such as the TONE series available from Union Carbide, Danbury, Conn. Polythioether polyols are also useful.

To obtain stable dispersions in hydro-alcohol systems, the non-ionic stabilizer is generally present in the polyurethane polymer from 5 to 30%, preferably 7 to 30% and most preferably about 10 to 20% by weight. The amount of non-ionic stabilizer will depend on the hydrophobicity of the prepolymer and the ratio of lower alcohol to water. In general, more hydrophobic prepolymers will require higher amounts of stabilizer.

Prepolymer Formation

The reaction of the components discussed above (i.e., the "A" component, the polyisocyanate, and the "B" component) to form the prepolymer will depend on their selection. Aromatic isocyanates are generally much more reactive than aliphatic isocyanates and may be reacted with polyols without the need for heat because the reaction will be exothermic. The prepolymer formation reaction may be run as 100% solids (i.e., little to no solvent) or may be carried out in an optionally polar organic solvent unreactive with the isocyanate. Such solvents include, for example, acetone, methyl ethyl ketone (MEK), methoxypropanol acetate (PM acetate), dimethyl acetamide, tetrahydrofuran, N-methyl-pyrrolidinone, and mixtures thereof. Preferably, the solvent used will not require removal in the final dispersion. It is also possible to incorporate solvents and/or plasticizers that are left in the prepolymer that become part of the finished dispersion.

When using preferred aliphatic isocyanates with polyfunctional alcohols, high solids concentrations and elevated reaction temperatures from about 50° C. to 80° C. are desirable so that high conversions of monomers to polymer can occur in a reasonable time, e.g., less than eight hours, preferably less than three hours. Preferred embodiments incorporating isophorone diisocyanate or hexamethylene diisocyanate and aliphatic primary or secondary alcohols are typically heated to about 80° C. for about 2 hours in the presence of a small amount of catalyst.

Useful catalysts include metal ligands, such as dibutyltin dilaurate and dibutyltin diacetate, and amines, such as triethylamine, DBU (1,8-diazabicyclo[5.4.0]undec-7-ene), and DABCO (1,4-diazabicyclo[2.2.2]octane), in useful concentrations of from about 0.01 to 1.0 mole percent (relative to the isocyanate reagent). Preferred catalysts are non-irritating and non-sensitizing to skin. Most preferred catalysts are those that can become bound to the polymer backbone and are thus non-leachable, such as FASTCAT 4224 from Elf Atochem North America, and certain alcohol and amine functional tertiary amine catalysts such as methyldiethanolamine and tetramethylguanidine. In batch preparations from about 100 to 1000 grams, about 0.1 gram of FASTCAT 4224 per 100 gram of total resin is used.

The ratio of polyisocyanate to polyol is adjusted such that the prepolymer has a molecular weight of about 1000 to 25000. The equivalents of polyisocyanate preferably exceed the total equivalents of polyol (i.e., total equivalents of active hydrogen), the equivalent excess being preferably from 0.1 to 5, more preferably 0.5 to 2, and most preferably from 0.8 to 1.2.

Prepolymer viscosity should be kept relatively low to facilitate dispersing in the hydro-alcohol solvent system. In general, the prepolymer viscosity should be less than about 250,000 centipoise (cps), preferably less than about 150,000 cps, more preferably less than about 100,000 cps and most preferably less than about 75,000 cps as measured at 23° to 25° C. using a Brookfield RVT rotovisco viscometer (Brookfield Engineering Laboratories, Stoughton, Mass.). Alternatively or additionally, the prepolymer may be heated or solvent may be added to lower the viscosity.

Chain Extending

Once the prepolymer is formed, the molecular weight should be increased to yield a dispersion with the desired properties. This step is accomplished by reacting the prepolymer with a "chain extender." As used herein the term "chain extender" means a polyactive hydrogen compound having a functionality of about 2 to 4, more preferably 2 to 3, and most preferably about 2 and generally having a molecular weight of about 30 to 2000, preferably 30 to 1000. Preferred chain extenders are polyfunctional alcohols, polyfunctional amines, or carboxylic acid hydrazides. Most preferred chain extenders are polyfunctional amines and carboxylic acid hydrazides.

Useful polyfunctional amines include: ethylenediamine; 1,6-diaminohexane, piperazine; tris(2-aminoethyl)amine; and amine terminated polyethers such as JEFFAMINE D230 and JEFFAMINE D400 from Huntsman Corporation, Salt Lake City, Utah.

Useful carboxylic acid hydrazide include adipic acid dihydrazide and oxalic acid dihydrazide. Particularly useful polyfunctional alcohols include alkylene diols having 2 to 24 carbon atoms such as ethylene glycol; 1,4 butane diol; and 1,8 octane diol. Useful polythiols include 1,2-ethanedithiol; 1,4-butanedithiol; 2,2'-oxytris(ethane thiol) and di- and tri-mercaptopropionate esters of poly (oxyethylene) diols and triols. Water is also useful as a chain extender as it reacts with isocyanate to form an unstable carbamic acid, which loses carbon dioxide to liberate an amine. This amine is then available to react with another isocyanate. When water is used as the chain extender, catalysts such as bis(dialkylaminoethyl) ethers should be used that preferentially accelerate the isocyanate/water reaction over the potential reaction between isocyanate and lower alcohol.

When the prepolymer has a functionality of 2 or less and the chain extender is difunctional, the ratio of isocyanate to active hydrogen in the chain extension step is preferably from about 0.6–1.2 to 1, more preferably from 0.75–1.0 to 1 and most preferably from 0.80–1.0 to 1 (except when water is used as the sole chain extender, in which case water can be present in large molar excess). When the prepolymer has a functionality higher than 2, due to the use of polyols or polyisocyanates with a functionality greater than 2, the ratio of isocyanate to active hydrogen present in the chain extender should be proportionately adjusted downward to prevent gelation.

The dispersions of the present invention are in water or alcohol-water with relatively high concentrations of a lower alcohol (typically more than 20:80 w/w alcohol to water). In this environment, endcapping of the isocyanate functional prepolymer may occur as the isocyanate reacts with the monofunctional alcohol solvent. Therefore, use of a polyfunctional amine as the chain extender is preferred because amines are much more reactive toward isocyanate than the lower alcohol, giving better control of molecular weight. For use on skin where irritation and/or sensitization is a concern, the most preferred ratio of isocyanate equivalents to amine equivalents is about 1:0.6–0.99 in order to ensure that little to no residual free amine remains in the final dispersion.

The reaction that forms the polyurethane polymer can be stopped by using chain termination species. The chain termination step is optional. Chain termination stops the growing polymer chain thereby controlling the molecular weight and the physical properties of the polymer. In one embodiment, a diamine chain extender is used in excess. The excess diamine functions as a chain terminator. Another useful chain terminating agent is 2-amino-2-methyl-1-propanol (AMP). It has been found that the chain terminators are useful when used to terminate generally less than about 15% of isocyanate groups on the prepolymer when used in combination with a difunctional chain extender such as ethylene diamine. Preferably, the chain terminators are used at levels of about 5% to 10% of the total isocyanate equivalents on the prepolymer, the rest being chain extended with a difunctional chain extender. Monofunctional amines or alcohols are useful as chain terminators. An example of a preferred monofunctional alcohol is ethanol, which can further function as part of the dispersing medium.

Preparation of Dispersion

The solvent used as the dispersing medium is selected from the group consisting, of a lower alcohol ($C_1$ to $C_4$ branched or straight chain aliphatic alcohol), water, and mixtures thereof. The preferred lower alcohols are ethanol, n-propanol, and 2-propanol (IPA). The most preferred solvents are water, IPA, ethanol, and mixtures thereof. The ratio of lower alcohol to water is generally greater than 50:50 by weight. Preferably the alcohol to water ratio is 60:40 to 90:10 w/w and more preferably the ratio is 70:30 to 85:15. In general, higher amounts of alcohol will result in a dispersion that exhibits faster dry times.

For certain dispersions, it was surprising to find that higher alcohol-water ratios result in lower viscosity dispersions. This result is surprising because at higher alcohol-water ratios, more of the polyurethane polymer would be expected to be solubilized, which would lead to an increase the viscosity. Thus, to achieve low viscosity dispersions at high alcohol-water ratios (i.e., ratios greater than 75:25), polyols that are insoluble in ethanol (i.e., solubility limit of less than 10% by weight in 200 proof ethanol) are used at concentrations in the prepolymer of at least 5%, preferably at least 10%, and most preferably at least 15% by weight, based on the total prepolymer weight. It has been found that at alcohol-water ratios greater than about 90:10, the polyurethane dispersion and the film produced therefrom tend to have lower tensile strength. It has also been found that secondary alcohol solvents, such as 2-propanol, yield films that have higher tensile strength when compared to films from primary alcohol solvents, such as ethanol.

The solvent system may also comprise additional solvents. For example, other rapid evaporating, skin compatible solvents may be used, such as hexamethyldisiloxane (HMDS); cyclic silicones ($D_4$ and $D_5$); $C_4$ to $C_{10}$ alkanes including isoparafins such as PERMETHYL 97A and ISOPAR C; acetone; hydrofluoroethers (HFEs) and the like. Certain HFEs, such as HFE 7100, have the added benefit in certain applications. When it is added to hydro-alcohol mixtures in levels above about 15 to 25% by weight, the composition becomes non-flammable.

To achieve rapid evaporation, it is preferred to use "low heat of vaporization solvents" i.e., solvents with heats of vaporization of less than about 150 calorie per gram (cal/g), preferably less than about 125 cal/g, more preferably less than about 100 cal/g and most preferably less than about 90 cal/g. For comparison purposes, water has a heat of vaporization of 540 cal/g, ethanol has a heat of vaporization of 204 cal/g, and isopropyl alcohol has a heat of vaporization of 159 cal/g. The low heat of vaporization solvents may be added to the solvent phase at levels of about 0 to 50%, preferably about 5% to 40%, and more preferably about 10% to 30% by weight of the solvent phase, provided that the low heat of vaporization solvent is miscible with the solvent phase at the given concentration. It has been found that when solvents such as HMDS (heat of vaporization of 44.3 cal/g) and ISOPAR C (heat of vaporization estimated to be about 87 cal/g) are added to the hydro-alcohol solvent mixtures having lower alcohol to water ratios of at least 70:30 at levels of 10% to 30% by weight, stable dispersions with very rapid dry times result.

The dispersions of the present invention may be prepared in any number of methods. In a first method, the prepolymer can be added to the alcohol-water solvent mixture as 100% solids or diluted first with a second solvent that may or may not be removed later. If the second solvent is to be removed, it is preferably more volatile than either water or the lower alcohol. In another method, the prepolymer can be dispersed in part of or in all of the alcohol-water solvent mixture or in a portion of it, with subsequent addition of additional solvents, which can be the same of different solvents. Any additional solvent added after dispersion is preferably added slowly in order to ensure the dispersion maintains stability. In yet another method, the prepolymer and/or dispersion solvent may be heated or cooled. In yet another method, the prepolymer may be dispersed in the alcohol-water solvent prior to, simultaneously with, or after the chain extender and chain terminator has been added to the solvent.

The preferred dispersion method involves heating the prepolymer to temperatures of about 45° to 80° C. to reduce its viscosity. The heated prepolymer is added to a rapidly stirring, high shear mixing apparatus, such as a homogenizer, containing the alcohol-water solvent. Thereafter, the polyamine chain extender is added at a predetermined rate, i.e., a controlled rate. Alternatively, for certain formulations, the polyamine can be added to the solvent mixture first and the heated prepolymer added to the rapidly mixing solvent mixture.

For an alcohol-water system, the level of lower alcohol is generally at least 20% by weight, preferably at least 40%, more preferably at least 60%, even more preferably at least 70% and most preferably at least 75% by weight. The level of lower alcohol preferably is not more than 95% and more preferably not more than 90% by weight. As used herein, "percent solids" is defined as the percentage of non-volatile components present in the dispersion at room temperature. The percent solids is generally taken as the sum weight of the "A" component, the isocyanate, and the "B" component, as well as any added chain extender, chain terminator, and other added non-volatiles such as plasticizers, continuous phase soluble polymers etc. The percent solids of the dispersion should be above about 15%, preferably greater than 25%, and more preferably greater than about 30%, most preferably greater than about 35%.

In one aspect of the present invention, films can be produced from the dispersion that have very little adhesion or tack to most surfaces such as skin, hair, and glass but have comparatively very high adhesion to themselves. When tested according to the test methods described herein, the ratio of adhesion to self to adhesion to glass is greater than about 2:1, preferably greater than about 3:1, more preferably greater than about 5:1 and most preferably greater than about 10:1. In certain embodiments, the ratio exceeds 20:1 and even 30:1 although such high ratios may not be required for all applications.

It has been found that one requirement for producing high self adhesive coatings is to control the molecular weight of the polyurethane in the final dispersion. The preferred weight average molecular weight is about 10000 to 50000, more preferably about 15000 to 35000 and most preferably about 20000 to 30000 daltons. When the molecular weight is too high, the resulting adhesive has very little self-adhesion. When the molecular weight is too low, the adhesive tends to have higher tack or adhesion to other substrates.

The molecular weight of the polymer in the final dispersion can be controlled in several ways. The first method concerns the alcohol to water ratio used as the dispersing medium. It has been found that for certain polymers, self-adhesion can be achieved at alcohol to water ratios in excess of about 75:25 wt/wt, preferably above 80:20, and more preferably at or above about 85:15. While not wanting to be bound by theory, it is believed that at higher alcohol to water ratios, more of the isocyanate reacts with the monofunctional alcohol solvent, thereby limiting the molecular weight. It is also believed that the higher alcohol ratios result in better solvation and dissolution of the prepolymer thereby also increasing the likelihood of reaction of the isocyanate groups with the monofunctional lower alcohol solvent.

The molecular weight of the prepolymer can also be controlled by the type of alcohol used as the solvent. Primary alcohols, such as ethanol, may result in higher self-adhesion than secondary alcohol solvents such as iso-propanol.

The molecular weight of the prepolymer can be further controlled by the process of dispersion and the process of adding the chain extender. At the current time, it is believed that dispersing the prepolymer in the solvent first, followed by amine addition (as the chain extender) at slower rates, can also improve the level of self-adhesion. A slow amine addition rate, however, can increase the level of tack.

The presently preferred method of controlling the level of self-adhesion is with the use of mono-functional amines added prior to or during the chain extension step. This method will result in end capping of some isocyanate groups thereby limiting the molecular weight. The mono-functional amines generally have the following structure:

$$R_1R_2NH$$

where $R_1$ and $R_2$ are independently H or $C_1$ to $C_{22}$ alkyl; $C_6$ to $C_{28}$ aryl, or $C_6$ to $C_{28}$ aralkyl optionally substituted in available positions by N, O, and S, including alcohol tertiary amine, quaternary amine, ketone, and carboxylic acid substitutions. Preferred mono-functional amines are those that would have low skin irritation if left unreacted in the formulation, such as 2-amino-2-methylpropanol or higher alkyl primary and secondary amines as well primary and secondary alkanolamines. Monofunctionaly alcohols or mercaptans may also be used to control the molecular weight but these are generally added to the prepolymer prior to dispersion and chain extension.

The level of ionic stabilizer may also effect self-adhesion. At the current time, it is believed that higher levels of stabilizer may result in lower self-adhesion.

Anti-Microbial Agents

Anti-microbial agents may be added to the prepolymer or to the solvent mixture (prior to or after dispersion formation). Suitable anti-microbial agents include (i) those listed in U.S. Pat. No. 5,951,993 Col. 21 lines 12 to 45; (ii) iodine-iodide combinations; (iii) antifungal agents, such as the "azoles," including but not limited to miconazole nitrate, ketoconazole, econozole, clotrimazole, and the like; (iv) tolnaftate; and (v) undecylinic acid and the like. Antibiotics may also be incorporated including combinations of antibiotics such as the popular triple antibiotic neomycin-polymyxin B-bacitracin. Preferred anti-microbial agents in anionic polyurethane dispersions include iodine-sodium iodide; iodine-potassium iodide; iodine-iodide complexes (so called iodophors), such as povidone-iodine and complexes with polyethylene oxide adducts.

The lower alcohol used to disperse the polyurethane polymer can impart anti-microbial properties to the dispersion. The amount of alcohol, however, should be at a sufficiently high concentrate in order to achieve anti-microbial activity. Generally, in order to achieve rapid kill of microbes, the lower alcohol (particularly, ethanol or IPA) to water ratio should be 60:40 to 90:10 by weight.

Additives

The formulations of the present invention may also include plasticizers that can be added either to the prepolymer directly or can be added to the solvent mixture. The use of plasticizers may allow for the use of less solvent, and therefore produce more rapidly drying films. Where plasticizers are used, the prepolymer should be formulated ensure the plasticized film has sufficient tensile strength. This could require the use lower molecular weight polyols (lower NCO equivalent weight prepolymers). Preferred plasticizers are cosmetically acceptable emollients such as those disclosed in U.S. Pat. No. 5,951,993 at column, 17 line 35 to column 21, line 6, which is hereby incorporated by reference.

Other compounds may be added to enhance or obtain particular properties, provided they do not interfere with the coating, and film forming properties. The dispersion may contain defoaming agents. Particularly useful defoaming agents include, e.g., Surfynol™ DF 110L (a high molecular weight acetylenic glycol nonionic surfactant available from Air Products & Chemicals, Inc.), SWS-211 (a silicone additive available from Wacker Silicone Corp), Dehydran™ 1620 (a modified polyol/polysiloxane adduct available from Henkel Corp.), Additive 65 (a silicone additive available from Dow Corning).

The dispersion may also contain flow and leveling agents such as Igepal™ CO-630 (an ethoxylated nonylphenol nonionic surfactant available from Rhone-Poulenc Surfactant & Specialty Div.), FLUORAD FC-171 (a nonionic surfactant available from 3M Company), FLUORAD FC-430 (a nonionic surfactant available from 3M Company), and Rexol™ 25/9 (an alkyl phenol ethoxylate nonionic surfactant available from Hart Chemical Ltd). Optionally, the dispersion may contain rheology modifiers such as the associative thickeners Acrysol™ RM-825, Acrysol TT-935 all available from Rohm and Haas company.

To increase the service life of the coatings generated from these dispersions, especially in outdoor applications, photostabilizers can be added. Useful photostabilizers include Tinuvin™ 400, (a hindered amine light stabilizer), Tinuvin™ 292 (a hindered amine light stabilizer), both commercially available from Ciba-Geigy Ltd. Also, antioxidants, such as IRGANOX 245 available from Ciba-Geigy Ltd., and Naugard-445, a 4,4'-bis ($\alpha\alpha$ dimethylbenzyl) diphenylamine, available from Uniroyal Chemicals can be added. For applications subjected to ultraviolet light (UV) degradation, at least about 0.1 parts by weight of the UV light stabilizer per 100 parts by weight polyurethane dispersion can be used to inhibit and retard the yellowing and photo degradation. Typically about 0.1 to 10 parts, preferably about 1 to about 10 parts are used per 100 parts of the polyurethane dispersion.

Test Methods

Dry Time and Cure Time

Dry time and cure time of the inventive polyurethane dispersion provide an indication of the amount of time required for dispersion, once coated, to form a film. Dry time was measured by coating the dispersion at a wet thickness of about 0.006 inch (0.15 mm) onto a preheated release liner.

The liner is polypropylene coated paper release liner from Schoeller Technical Papers, Inc., Pulaski, N.Y. as product designation: #57 lb MUL polypropylene coated one (1) side paper liner. Referring to FIG. 1, the liner 10 is placed on a heated plate 12. The temperature on the heated plate is controlled by passing water from a water bath 14 through the plate by using hose 16. Typically, the water can transferred using a pump. A temperature recorder 18 is used to monitor the surface temperature of the heated plate. The hose runs through the core of the plate in a serpentine fashion. Immediately after the dispersion (not shown) was coated on the liner, a measurement device 20 is placed on top o f the coated dispersion.

Figure 2:
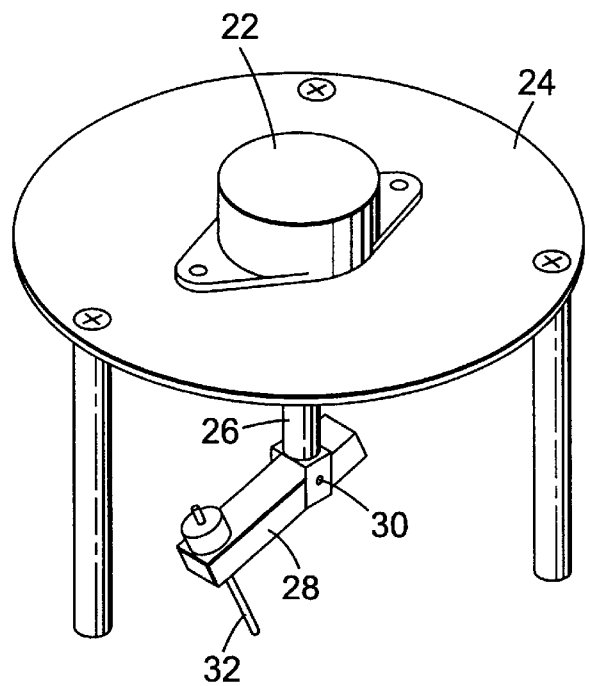
FIG. 2 is a schematic diagram of a measurement tool for measuring dry time and cure time of the present invention.

As shown in FIG. 2, the measurement device 20 contains a motor 22 that revolves at a speed of about 4 revolutions per hour. The motor is mounted on a small table 24 with a shaft 26 oriented in a vertical position. Connected to the shaft is a 1.5 inch arm 28. The arm lies on a pivot 30, allowing the arm to float up and down. At the tip of the arm is a 0.125 inch diameter stylus 32 rounded at the tip that rests on the wet dispersion, which is undergoing the drying process to form a film. The stylus weighs about 10 grams including the weight of the arm. The measurement device described herein is similar in design to a commercial device from the Gardner Company, Pompano Beach, Fla. as the "Dual Speed 'Bi-Cycle' Drying Time Recorder."

As the motor revolves, the stylus drags through the drying dispersion. Once the wake in the drying dispersion stopped (i.e., the stylus is no longer riding against the release liner but is riding on top of the film formed by drying of the dispersion), the film was considered "dry." Using a drying time recorder, not shown, the dry time (usually in seconds) can be estimated. The drying time recorder used herein is similar in design to the "Dual Speed Drying Time Recorder" from Gardner Company. The film's "cure time" can also be estimated. It is the time at which the stylus begins to ride on top of the entire thickness of the dried composition. At this point the film had enough integrity to be removed from the release liner in substantially one piece.

Dispersion Appearance

In some of the Examples below, the visual appearance of the dispersion was recorded. The various categories used to describe the dispersion include the following: almost clear; opaque; opaque white; and hazy yellow. The appearance is a qualitative assessment that a dispersion and not a solution was formed, i.e. that there is some level of insoluble dispersed phase.

Minimum Bactericidal Concentration Test

Selected examples were tested for the Minimum Bactericidal Concentration (MBC). Two MBC's for each example was done. One MBC used *Staphylococcus aureus* ATCC 14154 as the organism and the second MBC used *Escherichia coli* ATCC 8739.

To test for MBC, one gram of dispersion prep was weighed out on the bottom of a graduated cylinder which was brought up to 10 milliliter (ml) with either 85:15 ethanol-water or 85:15 IPA-water matching the solvent in the dispersion. The contents were mixed well with a glass stir rod. The cylinders were then capped. A 0% PVP-iodine placebo sample was also prepared in the same manner. Control samples of PVP-iodine USP in alcohol-water of the same percentage were prepared. Final dilutions were made with water to bring the concentration of available iodine down to 32 microgram per ml. Two hundred microliter ($\mu$l) aliquots were placed in a 96 well plate and serially diluted two-fold with sterile water. The sample, placebo, and control were run on the same plate. After the samples were serially diluted, 100 $\mu$l of the organism suspension was added to each well. The timer was started for 30 minutes after inoculation of the last well. The plate was placed in the incubator at 37° C. for 30 minutes. At 30 minutes, 2 $\mu$l aliquots were transferred from each well into a neutralizer plated that contained 0.1% sodium thiosulfate, which neutralized iodine activity. This neutralized plate was incubated overnight and read the following day.

EXAMPLES

The following examples further illustrate various specific features, advantages, and other details of the invention. The particular materials and amounts recited in these examples, as well as other conditions and details, should not be construed in a manner that would unduly limit the scope of this invention. Percentages given are by weight, unless otherwise specified.

Example 1

Effect of Solvent Type and Solvent Concentration on the Dispersion

A. Preparation of Sulfopolyester Diol

A mixture of (i) dimethyl 5-sodiosulfoisophthalate (DMSSIP, 295.9 g, 2 equivalents, 295.9 equivalent weight, available from E. I. DuPont de Nemours, Wilmington, Del.); (ii) diethylene glycol (DEG, 371.5 g, 7 equivalents, 106.2 equivalent weight, available from Aldrich Chemical Co., Milwaukee, Wis.); and (iii) zinc acetate, (0.67 g, available from Aldrich) was heated to about 180° C. for about 5 hours in a 2 liter, three-neck glass flask equipped with a Dean-Stark trap, dry ice condenser, and a nitrogen bleed. The methanol by-product was distilled from the reaction mixture.

Dibutyltin dilaurate (0.74 g, available from available from Alfa Chemical Co., Ward Hill, Mass.) was added to the above reaction product, the temperature held at about 180° C. Epsilon-caprolactone (570.6 g, 10 equivalent, 114.1 equivalent weight, available from Aldrich) was added portion-wise over about a 30 minute period. When addition was complete, the reaction mixture was held at about 180° C. for 4 hours. The product is designated as "2:7:10" sulfopolyester diol, because the molar ratio of the amounts of DMSSIP:DEG:caprolactone is 2:7:10. This diol, which had an equivalent weight of 350 g/eq OH, is one of the useful B components.

B. Prepolymer Formation

Into a one-liter heated, nitrogen purged, reaction flask equipped with an overhead air stirrer was charged the following components: (i)140 g KRATON L-2203 hydrogenated polybutadiene diol (OH equivalent wt 1660) from Shell Chemical Co., Houston, Tex.; (ii) 318 g TERATHANE 2000 polytetramethylene oxide diol (OH equivalent wt 1031.3) from E.I. du Pont Co., Wilmington, Del.; (iii) 56 g of the 2:7:10 sulfopolyester diol prepared in Part I above, and (iv) 14 g SURFYNOL 104 surfactant from Air Products, Lehigh Valley, Pa. (OH equivalent wt 113.2). The mixture was heated to about 80° C. About two (2) drops of dibutyl tin dilaurate from Aldrich Chemical was added. Then, 120.6 g DESMODUR I was added. The reaction temperature peaked to about 88° C. The resulting mixture was the isocyanate terminated prepolymer.

C. Dispersion Formation

The above prepolymer was made into a polyurethane dispersion in an alcohol-water solvent mixture as follows. The alcohol used was isopropyl alcohol. Dispersions were prepared by mixing together alcohol and water in a 200-ml jar equipped with an overhead stirrer and a baffle to ensure good mixing. The radial high shear stirrer entered the jar at an angle to further ensure good mixing. The alcohol-water mixtures were at room temperature.

The prepolymer was heated to about 60° C. to reduce the viscosity. The weight of prepolymer was placed in a syringe and delivered to the rapidly mixing alcohol-water mixture. Using a syringe pump, ethylene diamine (EDA, a chain extender, from Aldrich Chemical Co.) was added at a controlled rate of about 0.071 ml/min to 90% of the theoretical value of isocyanate in the prepolymer. The NCO to amine ratio was fixed at about 0.9 to ensure that little to no residual EDA remained after the reaction. The dispersions were mixed during the entire addition time and for an additional 10 minutes. All dispersions were made at a total batch size of about 175 g. The weight percent solids (i.e., wt % polyurethane) were varied as described in the Table 1 below.

About 8 to 16 hours after the dispersion was made, the viscosity was measured on a Brookfield LVT viscometer. Samples of the dispersions were knife-coated onto a silicone release liner to a target dry thickness of about 0.001 inch (1 mil or 0.025 mm), except where noted in order to show the effect of thickness on the tensile and elongation. The gap used and the actual thickness to achieve a 0.001 inch thick dry film varied from approximately 0.005 to 0.007 inch (0.13 to 0.18 mm). The coated dispersion samples were allowed to dry overnight (at least 14 hours and usually 24 hours) at ambient conditions. The tensile and elongation properties of the samples were measured on 2.54 cm wide samples. The samples were cut while still on the coating liner and with an additional piece of liner on top. Using an INSTRON model 4400R from Inston Corporation Canton, Mass. at a gauge length of 2.54 cm, the samples were tested for peak load, tensile strength, and elongation at break using a pull speed of 10 inches/min (25.4 cm/min). The results are listed in Table 1.

The data in Table 1 illustrate the effect of percent solids and of the alcohol-water ratio on the dispersion viscosity and tensile strength. The data indicated that the viscosity of the dispersions at any given alcohol-water ratio increased as the percent solids of the dispersions increased. See, e.g., the viscosity data for Examples 1A to 1D, a 70:30 IPA-water dispersion. The increase, however, was much more dramatic at the lower levels alcohol-water. Compare, e.g., the viscosity data for Examples 1Q to 1T, at 90:10 IPA-water, with the viscosity data for Examples 1A to 1D.

The tensile strength decreased as the alcohol-water ratio increased. Compare, e.g., Examples 1A, 1E, 1I, 1M, and 1Q, all at 28% solids but at increasing IPA-water levels. Example 1Q (90:10 IPA-water) had a peak tensile strength of about 2.0 lb/in width., while Example 1A (70:30 IPA-water) had a peak tensile strength of about 4.9 lb/in width. While not intending to be bound by theory, it is presently believed that the tensile results are due to a reduction in ultimate molecular weight of the polyurethane because the alcohol (isopropyl alcohol) reacted with the isocyanate and end capped the polyurethane during the chain extension step. It is surprising that the tensile strength is maintained at high levels up to an IPA-water ratio of 85:15.

The particle size of certain dispersions was measured on a Coulter LS 100 laser Particle Size Analyzer equipped with a microvolume module. Usually, the particle size was measured one day after dispersions were made. The particle size was measured again about 30 days after the dispersions were made. During this period, the dispersions were sealed and stored at room temperature. Samples were diluted in the same solvent mixture as the original dispersion to make the measurement. The results are shown in Table 2 below, which indicate that the dispersions have mean particle sizes generally under about 5 to 6 micrometers ($\mu$m). All dispersions appear to be stable after about 30 days. The variance in the 90:10 IPA-water sample, however, appeared to have increased significantly.

TABLE 1

| Sample No. | % IPA wt % | % Solids | Viscosity Cps | Dry Thickness mil | Tensile Peak load Lbs | Tensile Strength lbs/mil | Elongation at break % |
|---|---|---|---|---|---|---|---|
| 1A | 70 | 28 | 2580 | 1.1 | 5.4 | 4.91 | 564 |
| 1B | 70 | 32 | 8875 | 1.1 | 5.7 | 5.18 | 554 |
| 1C | 70 | 36 | 28125 | 1.1 | 6.0 | 5.45 | 548 |
| 1D | 70 | 40 | 68750 | 1.4 | 7.0 | 5.00 | 542 |
| 1E | 75 | 28 | 3010 | 1.0 | 4.8 | 4.80 | 530 |
| 1F | 75 | 32 | 6750 | 1.1 | 5.3 | 4.82 | 551 |
| 1G | 75 | 36 | 20500 | 1.0 | 5.6 | 5.60 | 550 |
| 1H | 75 | 40 | 60250 | 1.2 | 5.6 | 4.67 | 506 |
| 1I | 80 | 28 | 1910 | 1.0 | 4.4 | 4.40 | 548 |
| 1J | 80 | 32 | 4700 | 1.0 | 5.1 | 5.10 | 568 |
| 1K | 80 | 36 | 16175 | 1.0 | 4.4 | 4.40 | 511 |
| 1L | 80 | 40 | 43190 | 1.2 | 6.4 | 5.33 | 545 |
| 1M | 85 | 28 | 1040 | 1.1 | 3.8 | 3.45 | 563 |
| 1N | 85 | 32 | 2900 | 0.9 | 4.2 | 4.67 | 566 |
| 1O | 85 | 36 | 7500 | 1.0 | 4.2 | 4.20 | 535 |
| 1P | 85 | 40 | 21500 | 1.2 | 5.8 | 4.83 | 567 |
| 1Q | 90 | 28 | 460 | 1.0 | 2.0 | 2.00 | 545 |
| 1R | 90 | 32 | 1065 | 1.0 | 2.0 | 2.00 | 554 |
| 1S | 90 | 36 | 2450 | 0.8 | 1.6 | 2.00 | 524 |
| 1T | 90 | 40 | 5660 | 1.1 | 2.9 | 2.64 | 571 |
| 1U | 70 | 40 | 68750 | 0.5 | 2.8 | 5.60 | 500 |
| 1V | 70 | 40 | 68750 | 1.4 | 7.0 | 5.00 | 542 |
| 1W | 70 | 40 | 68750 | 2.6 | 12.6 | 4.85 | 566 |
| 1X | 70 | 40 | 68750 | 3.9 | 15.2 | 3.90 | 539 |

TABLE 2

Particle Size Analysis of Various Samples

| Sample No. | % IPA | Mean Diameter (μm) Day 1 | Variance Day 1 | Mean Diameter (μm) Day 30 | Variance Day 30 |
|---|---|---|---|---|---|
| 1D | 70 | 3.6 | 3.2 | 4.0 | 4.7 |
| 1H | 75 | 3.6 | 4.0 | 3.3 | 3.2 |
| 1L | 80 | 5.6 | 6.0 | 3.6 | 4.6 |
| 1P | 85 | 5.6 | 6.2 | 3.3 | 3.8 |
| 1T | 90 | 5.6 | 3.4 | 5.0 | 25.7 |

Addition of Anti-microbial Agents

To sample 10 in Table 1, povidone-iodine (PVP-iodine USP), from BASF Co., was added at 2.5%, 5%, and 7.5% by weight (e.g., 2 grams PVP-iodine USP added to 38 g of dispersion to make a 5% composition. The PVP-iodine was allowed to dissolve. The tensile and elongation results are shown below.

TABLE 3

PVP-Iodine in Sample 10

| PVP (wt %) | Tensile Strength (lb/in width) | Elongation at break (%) |
|---|---|---|
| 0 | 4.2 | 535 |
| 2.5 | 3.8 | 517 |
| 5.0 | 3.8 | 474 |
| 7.5 | 4.3 | 438 |

The results in the above table indicate that the tensile strength was not significantly effected but there does appear to be a decrease in the elongation with increasing amounts of PVP-iodine.

Anti-microbial Agents in Dispersions with Varying Alcohol-water Ratio

A second set of dispersions was prepared containing 5 wt % PVP-iodine USP. All dispersions were at 36% solids. The IPA-water ratio was varied as shown in Table 4. The results showed a trend that the lower the IPA-water ratio, the higher the tensile strength. The elongation does not appear to be appreciably effected.

TABLE 4

PVP-Iodine at Various IPA-Water Ratios

| IPA:Water Ratio | Dry Thickness (mil) | Mean Tensile (lb/in width) | Mean Elongation at Break (%) |
|---|---|---|---|
| 90:10 | 1.0 | 2.37 | 447 |
| 85:15 | 1.1 | 3.75 | 474 |
| 80:20 | 1.2 | 4.51 | 453 |
| 75:25 | 1.1 | 4.77 | 488 |

Polyurethane Dispersions in Ethanol-Water Solvent Systems

A truncated duplicate set of dispersions of Examples 1A to 1X were prepared except that the IPA was replaced with ethanol (EtOH), as shown below. All dispersions were made at about 40% solids.

TABLE 5

Polyurethane Dispersions in Ethanol-Water System

| EtOH:Water Weight ratio | Dry Thickness Mil | Tensile (peak load) (lbs) | Tensile (lbs/in width) | Elongation at break (%) |
|---|---|---|---|---|
| 90:10 | 1.1 | 0.43 | 0.39 | 472 |
| 85:15 | 1.2 | 1.1 | 0.92 | 680 |
| 80:20 | 1.1 | 1.6 | 1.45 | 630 |
| 75:25 | 1.1 | 3.0 | 2.72 | 652 |
| 70:20 | 1.0 | 3.3 | 3.3 | 652 |

Dry Time and Cure Time of Sample 1G

Sample 1G, which was a 75:25 IPA-water polyurethane dispersion at 36% solids, was coated at 0.006 inch wet thickness four different times to determine the dry time and cure time at various surface temperatures. All samples had a dry thickness of about 0.0011 to 0.0013 inch.

TABLE 6

Dry Time and Cure Time for Sample 1G

| Temperature of heated plate (° C.) | Dry Time (seconds) | Cure time (seconds) |
|---|---|---|
| 28 | 135 | 207 |
| 30 | 120 | 195 |
| 32 | 90 | 165 |
| 34 | 78 | 138 |

Comparative Examples A and B

As stated, it is desired that the inventive dispersion have a short dry time and short cure time. These two comparative examples are used to show the difference in performance between a polyurethane dispersion and a polymer solution. In Comparative Example A, a polymer solution was made as follows. Into a reaction vessel was charged: about 30 g of cellulose acetate propionate (CAP 504-0.2 from Eastman Chemical Co., Kingsport, Tenn.); about 15 g of glycerin triacetate (TRIACETIN, from Eastman Chemical Co.); and about 2 grams of diisooctylphthalate (DIOP, from Eastman Chemical Co.) to form the solution. The latter two components were added to plasticize the CAP. Without the plasticizers, the polymer films formed would be very brittle.

In Comparative Example B, a polymer solution was made as follows: to a reaction vessel, about 50 g of AIRFLEX 410 (believed to be a 55% solids polyvinylacetate dispersion in water from Air Products Co., Allentown, Pa.) was dissolved in about 70 g of 90:10 EtOH-water solvent system.

Both solutions were coated onto the polypropylene-coated liner described in the Dry Time test method at a wet thickness of 0.006 inch (0.15 mm). The heated plate was set at a temperature of about 32.5° C. The film made from Comparative Ex. A solution had a dry time of about 132 seconds, tensile strength of 0.37 lb/in width, and an elongation at break of 70%. The film made from Comparative Ex. B solution had a dry time of 450 seconds, tensile strength of 2.2 lb/in width, and an elongation at break of 7%. Comparative Ex. A had a relatively short dry time but had very poor tensile strength compared to Example 1. Comparative Ex. B had higher tensile strength, but would be considered to have an unacceptably long dry time compared to Example 1.

Example 2

Anionic Carboxylic Acid Stabilized Polyurethane Dispersion

To prepare such a dispersion, a sample of dimethylolpropionic acid (DMPA, also called 2,2 Bis (hydroxymethylpropionic acid from Aldrich) was dissolved at 30% by weight in N-methyl-2-pyrrolidinone (NMP, from Aldrich). This mixture was used to prepare the following prepolymer which had an NCO/OH ratio of about 1.99.

TABLE 7

Components for the Prepolymer

| Product Name | Component | Eqwt (g/eq) | Weight (g) |
|---|---|---|---|
| DESMODUR W | $H_{12}MDI$ | 132.2 | 265.9 |
| 30% DMPA-NMP mixture | | | 106.53 |
| ACCLAIM 3201[a] | polypropylene glycol | 1488.1 | 212.5 |
| ACCLAIM 3201[a] | polypropylene glycol | 1524.5 | 134.59 |
| PPG1025[a] | polypropylene glycol | 512.0 | 1555.32 |

[a]available from Lyondell Co., Houston TX.

In a heated, continuously nitrogen purged stirred reactor, all components except the DESMODUR W were combined and mixed. Once the contents reached about 80° C., half of the DESMODUR W was added along with 8 drops of dibutyltin dilaurate followed by the rest of the DESMODUR W. The reaction temperature decreased briefly to about 68° C. and then rose to about 83° C., at which time the prepolymer appeared visually clear.

This prepolymer was mixed for about 90 minutes, allowed to cool, and sealed under nitrogen. The prepolymer was relatively low in viscosity (i.e., it flowed) and contained about 91.5% solids (i.e., 8.5% NMP). The prepolymer was used to prepare dispersions at various ethanol-water ratios.

When preparing the ethanol-water dispersions, potassium hydroxide was used to neutralize the DMPA to yield an anionic form. The dispersions were made in a manner similar to that described in Example 1, except that KOH was added to the ethanol-water prior to any prepolymer addition and the EDA was added drop-wise over a 2 minute period. About 90% of the theoretical molar equivalent of EDA was used in order to ensure very low to no residual levels.

TABLE 8

| Example→ | 2A | 2B | 2C | 2D | 2E |
|---|---|---|---|---|---|
| Prepolymer (g) | 75 | 75 | 75 | 75 | 75 |
| Ethanol (g) | 40.8 | 0 | 51.0 | 54.4 | 0 |
| IPA (g) | 0 | 40.8 | 0 | 0 | 40.8 |
| Water (g) | 27.2 | 27.2 | 17 | 13.6 | 27.2 |
| 4N KOH (g) | 6.82 | 6.82 | 6.82 | 6.82 | 6.82 |
| WD4006 (g) | 0 | 21.4 | 0 | 0 | 0 |
| EDA (g) | 2.54 | 2.54 | 2.54 | 2.54 | 2.54 |
| RESULTS: | | | | | |
| Peak Tensile (lb) | 0.88 | 0.87 | 0.72 | 0.85 | 2.57 |
| Tensile strength (lb/in width) | 0.37 | 0.37 | 0.36 | 0.41 | 0.51 |
| Elongation (%) | 44.9 | 69 | 46.0 | 42.3 | 66.4 |
| Film Thickness (mil) | 2.4 | 2.3 | 2.0 | 2.1 | 5.0 |

After adding the prepolymer, each example was adjusted to a pH of about 7.0. To Example 2B was added a 40% solids, water based polyurethane pressure sensitive adhesive (PSA) (WD4006 from H.B. Fuller, St. Paul, Minn.). The PSA was added to increase adhesion to skin. The PSA was added to the alcohol-water solvent system prior to prepolymer addition. The EDA was added and the reaction mixture stirred at high speed for 20 minutes. Stable dispersions were obtained in call cases.

Example 2A was an opaque, white, low viscosity dispersion. Example 2B was opaque and very viscous. Example 2C was opaque, low viscosity dispersion. Example 2D was off white, but turned clear and was of low viscosity. Film samples were prepared and tested. The results are in the table above. The tensile strength and elongation properties of these materials were significantly lower than those of Ex 1.

Three additional prepolymers were prepared, as shown in Table 9, also using DMPA as the stabilizer.

TABLE 9

| Component | Eqwt (g/eq) | Amount (g) Prepolymer A | Amount (g) Prepolymer B | Amount (g) Prepolymer C |
|---|---|---|---|---|
| NCO/OH | NA | 2 | 2 | 2.1 |
| NCO Equivalent wt | NA | 799 | 659 | 624 |
| DESMODUR W | 132.2 | 66.2 | 80.2 | 80.95 |
| Arcol LHT 42[a] | 1368 | 93.74 | 0 | 0 |
| PPG 1025[b] | 512 | 32.1 | 76.5 | 76.73 |
| DMPA | 67.1 | 8 | 8 | 8 |
| ACCLAIM 2200[b] | 1018.2 | 0 | 35.3 | 0 |
| ACCLAIM 3201[b] | 1524.5 | 0 | 0 | 34.32 |

[a]polypropylene glycol triol from Lyondell Chemical Co. Houston TX
[b]polypropylene glycol diol from Lyondell Chemical Co.

The DMPA was added as a 30% solution in NMP, as described above. The reaction was conducted as above including the addition of about three (3) drops of dibutyltindilaurate to catalyze the urethane reaction. Dispersions were made using these prepolymers as described above except that 1N NaOH was used to neutralize the DMPA. The following dispersions were prepared.

TABLE 10

| Example→ | 2F | 2G | 2H | 2I | 2J | 2K | 2L |
|---|---|---|---|---|---|---|---|
| Alcohol-Water ratio | 75:25 | 85:15 | 85:15 | 75:25 | 75:25 | 25:75 | 75:25 |
| % solids | 41.5 | 40.0 | 41.2 | 35.5 | 38.0 | 39.6 | 32.4 |
| Prepolymer A (g) | 0 | 0 | 0 | 0 | 0 | 29.7 | 18.2 |
| Prepolymer B (g) | 0 | 0 | 40 | 34.8 | 37.6 | 0 | 0 |
| Prepolymer C (g) | 51.2 | 47.8 | 0 | 0 | 0 | 0 | 0 |
| 1N NaOH (g) | 13.9 | 13 | 10.9 | 9.5 | 10 | 8.0 | 6.8 |
| EtOH:$H_2O$ | 50.1 | 0 | 0 | 48 | 46 | 30 | 30 |
| IPA:$H_2O$ | 0 | 47.8 | 40 | 0 | 0 | 0 | 0 |
| EDA | 1.6 | 1.5 | 1.5 | 1.4 | 1.4 | 0.92 | 0.60 |
| RESULTS: | | | | | | | |
| Peak Tensile (lb) | 14.8 | 5.1 | 14.6 | 3.5 | 2.88 | | |
| Tensile (lb/in width) | 2.7 | 1.75 | 3.1 | 1.8 | 1.44 | | |
| Elongation (%) | 680 | 536 | 421 | 233 | 42 | | |
| Thickness (mil) | 5.5 | 2.9 | 4.7 | 1.9 | 2.0 | | |

The dispersions 2F to 2J had good tensile and elongation properties. Examples 2F to 2K had cloudy to opaque white dispersions. Example 2L was slightly cloudy.

Example 3

Quaternary Ammonium Stabilized Polyurethane Dispersions

The following prepolymer was prepared which had an NCO/OH ratio of about 2.0 and a theoretical NCO equivalent wt of about 1058 g per equivalent weight NCO. The prepolymer components included 24.8 g DESMODUR W (131.2 equiv. wt), 15 g VARIQUAT K1215 (PEG 2 cocomonium chloride—cationic stabilizing compound, 448 equivalent wt), and 60.2 g FOMREZ E65-56 (poly(hexamethylene-neopentyl) adipate polyester polyol, the "A" component). The prepolymer was prepared according to Example 1 except that the temperature was held at 75° C. for 3 hours and a reactive tin catalyst was used. The reactive catalyst ensures no leaching of tin onto or into the skin.

The reactive tin catalyst was dibutylin-(1-mercaptoethanol((1-thioglycerol), having an empirical formula $C_{13}H_{30}O_3S_2Sn$. It was made as follows. In a 500 ml round bottom flask fitted with a reflux condenser and a thermometer was charged with 11.72 g (0.15 mole) of 2-mercaptoethanol, 16.87 g (0.156 mole) of 3-mercapto-1, 2-propanediol, 37.34 g (0.15 mole) of dibutyltin oxide, and 250 ml of toluene. The mixture was thoroughly stirred and gently refluxed until the theoretical amount of water (2.7 ml) of reaction was collected in the Dean Stark water trap. After cooling, the solvent was stripped off under reduced pressure. The yield was 63.2 g of viscous liquid. Based on NMR analysis, the catalyst is essentially the structure shown below:

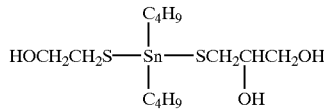

The VARIQUAT K1215 was thoroughly dried prior to use by mixing it with an equal volume of toluene in a 3-neck flask equipped with stirrer, Dean Stark trap with condenser, and a thermometer. The contents were heated to boiling and refluxed until no more water came over. The toluene was then stripped off using a rotary evaporator under vacuum and heated to a temperature of about 90° C. About 24 hours after the prepolymer was made, dispersion were made as shown in the following table.

TABLE 11

| Example→ | 3A | 3B | 3C | 3D |
|---|---|---|---|---|
| IPA:Water ratio | 90:10 | 85:15 | 80:20 | 75:25 |
| IPA (g) | 81 | 76.5 | 72 | 67.5 |
| Water (g) | 9 | 13.5 | 18 | 22.5 |
| Prepolymer (g) | 60 | 60 | 60 | 60 |
| EDA (g) | 1.53 | 1.53 | 1.53 | 1.53 |
| RESULTS: | | | | |
| Appearance | almost clear | hazy yellow | hazy yellow | Hazy yellow |
| Tensile (lb) | 5.6 | 6.2 | 6.5 | 5.4 |
| Tensile strength (lb/in width) | 5.6 | 6.2 | 6.5 | 5.4 |
| Elongation (%) | 400 | 688 | 619 | 490 |
| Thickness (mil) | 1 | 1 | 1 | 1 |

The dispersions of Examples 3A to 3D had good tensile strength and elongation.

Example 4

Quaternary Ammonium Stabilized Polyurethane Dispersion with Anti-microbial

The following two prepolymers were made in accordance with the procedure of Example 1.

TABLE 12

| | Equivalent wt. (g/eq) | Prepolymer D | Prepolymer E |
|---|---|---|---|
| NCO/OH | NA | 2 | 2 |
| NCO Equivalent wt | NA | 1117 | 1008 |

TABLE 12-continued

| | Equivalent wt. (g/eq) | Prepolymer D | Prepolymer E |
|---|---|---|---|
| DESMODUR W (g) | 132.2 | 47.3 | 52.5 |
| VARIQUAT· K1215 (g) | 446 | 20 | 40 |
| FOMREZ E65-56 (g) | 988.9 | 132.7 | 107.6 |

After making the prepolymers, on cool down, 50 g of methylethyl ketone was added to each one to yield an 80% solids prepolymer. In a sealed jar, they were heated to 100° C. for one hour and then cooled on a roller for 3 hours. The viscosities of these prepolymers were measured on a Brookfield Engineering Laboratories (Middleboro, Mass.) LVT Rotoviscometer using spindle #2 at room temperature, about 23° C. The viscosity of prepolymer D was about 1200 cps and the viscosity of prepolymer E was about 920 cps. Dispersions were prepared from prepolymers D and E as shown in the following table.

TABLE 13

| Example→ | 4A | 4B | 4C | 4D |
|---|---|---|---|---|
| EtOH:H$_2$O ratio | 40:60 | 60:40 | 60:40 | 40:60 |
| EtOH:H$_2$O (g) | 21.5 | 21.5 | 12.9 | 37.4 |
| Prepolymer D (g) | 12.5 | 12.5 | 12.5 | 0 |
| Prepolymer E (g) | 0 | 0 | 0 | 12.5 |
| EDA (g) | 0.27 | 0.27 | 0.27 | 0.30 |

About 24 hours after the dispersions were made, the following observations were recorded. All dispersions appeared white and creamy in consistency. Example 4A was smooth and flowing. Example 4B was quite thick but stable and flowed. Example 4C was a very thick paste and somewhat stringy. Example 4D was thick and creamy but flowed.

A 20.1% (w/v) solution of chlorhexidine gluconate antimicrobial agent was added into Ex. 4A at a CHG concentration of 1% by weight. The CHG was mixed in rapidly for 2 minutes to produce a very smooth fluid.

A 20.1% (w/v) solution of chlorhexidine gluconate antimicrobial agent was added into Example 4A at a CHG concentration of 2% by weight. The CHG was mixed in rapidly for 2 minutes to produce a very smooth fluid.

Example 5

Quaternary Ammonium Stabilized Polyurethane Dispersion using KRATON L2203 Polyol and added Polymer The following isocyanate terminated prepolymer (having an NCO/OH of 2 and NCO equivalent of 1246) was produced in accordance with the general procedure of Example 1, but using the following components: 42.4 g DESMODUR W (132.2 equivalent wt), 40 g dried VARIQUAT K 1215 (446 equivalent wt), and 117.6 g KRATON L 2203 (alcohol-water insoluble polyol, 1660 equivalent wt).

About 96 g of the prepolymer was mixed with 30 g hexane to produce a 76% solids mixture which was creamy and opaque in appearance. The viscosity was measured as in Example 4 and found to be about 1600 cps. The mixture was used to make dispersions in 40:60 EtOH:H$_2$O solvent system to which had been added and dissolved CELQUAT SC 230M (a quaternary modified cellulose (polyquaternium 10) available from National Starch, Bridgewater, N.J.).

TABLE 14

| Example→ | 5A | 5B | 5C |
|---|---|---|---|
| Percent Solids | 23 | 27 | 24 |
| EtOH:H$_2$O (g) | 30 | 20 | 30 |
| Prepolymer (g) | 12.5 | 10.0 | 12.5 |
| CELQUAT SC 230M (g) | 0.15 | 0.05 | 0 |
| EDA (g) | 0.3 | 0.3 | 0.3 |

Example 5A dispersed well but had a very high, almost gel viscosity 24 hours after it was made. Example 5C, no CELQUAT, did not disperse but rather coagulated to large particulates floating on the top of the solvent. Example 5B, at reduced continuous phase soluble CELQUAT polymer, was a creamy smooth, opaque, relatively thick but flowable dispersion. This indicated that the continuous phase soluble polymer (in this case CELQUAT SC230M) aided in stability of the dispersion. This could be due to increased shear due to the increase in initial continuous phase viscosity, improved particulate stabilization due to steric and/or ionic effects, or both of the above.

Example 6

Effect of Added Iodine as an Anti-microbial Agent

The following prepolymers were prepared generally in accordance with the procedure of Example 1 except that the catalyst of Example 3 was used in place of dibutyltin dilaurate.

TABLE 15

| | (g/equiv) | Pre-polymer F | Pre-polymer G | Pre-polymer H |
|---|---|---|---|---|
| NCO/OH Ratio | | 1.99 | 2 | 2 |
| NCO Equivalent wt | | 1061 | 1008 | 1000 |
| DESMODUR W (g) | 132.2 | 148.8 | 52.5 | 0 |
| VARIQUAT K1215 (g) | 446 | 90 | 40 | 0 |
| FOMREZ E65-56 (g) | 984.7 | 361.2 | 107.6 | 0 |
| DESMODUR I (g) | 111.2 | 0 | 88.3 | 89 |
| KRATON L2203 (g) | 1660 | 0 | 60 | 0 |
| Himod sulfonated diol | 300 | 0 | 50 | 50 |
| PRIPLAST 3192 (g) | 1038.9 | 0 | 201.7 | 0 |
| TERATHANE 2000 (g) | 1020 | 0 | 0 | 187.3 |
| ACCLAIM 3201 (g) | 1484.1 | 0 | 0 | 73.8 |

The prepolymers were used to prepare dispersions in accordance with Example 1 except that the EDA was added at a rate of 0.175 mi/minute. The dispersions were tested for viscosity according to Example 4, were knife coated onto release liner to produce film samples, and film samples were tested. The dispersion formulations are shown below along with the results.

TABLE 16

| Example→ | 6A | 6B | 6C |
|---|---|---|---|
| IPA:H$_2$O Ratio | 80:20 | 70:30 | 90:10 |
| Percent solids | 40 | 40 | 40 |
| Prepolymer F (g) | 60 | 0 | 12.5 |
| Prepolymer G (g) | 0 | 60 | 0 |
| Prepolymer H (g) | 0 | 0 | 60 |
| IPA (g) | 72 | 63 | 81 |
| Water (g) | 18 | 27 | 9 |
| EDA (g) | 1.53 | 1.61 | 1.62 |

TABLE 16-continued

| Example→ | 6A | 6B | 6C |
|---|---|---|---|
| RESULTS: | | | |
| Viscosity (cps) | 17100 | 15425 | NA |
| Tensile (lb) | 2.4 | 3.8 | 2.7 |
| Tensile strength (lb/in width) | 2.2 | 3.5 | 2.5 |
| Elongation (%) | 789 | 626 | 1022 |
| Thickness (mil) | 1.1 | 1.1 | 1.1 |

To 47.5 g of Example 6A was added 2.5 g of povidone-iodine USP (PVP-1) (BASF) and mixed in thoroughly until dissolved by rolling. To 47.8 g of Example 6A was added 1.0 g of iodine (I) and 1.2 g of sodium iodide (NOI) and these were dissolved by rolling. To 47.8g of Example 6B was added 1.0 g of iodine and 1.2 g of sodium iodide, and these were dissolved by rolling. To 47.5 g of Example 6C was added 2.5 g of povidone-iodine USP which was dissolved by rolling. These dispersions were tested and the results are shown below.

TABLE 17

| Example→ | 6D | 6E | 6F | 6G |
|---|---|---|---|---|
| Dispersion Used | 6A | 6A | 6B | 6C |
| Anti-microbial Added | 2.5 g PVP-I | 1.0 g I, 1.2 g NaI | 1.0 g I, 1.2 g NaI | 2.5 g PVP-I |
| Tensile (lb) | 2.1 | 2 | 2.7 | 2.4 |
| Tensile Strength (lb/in width) | 2.0 | 1.5 | 2.5 | 1.8 |
| Elongation (%) | 850 | 724 | 653 | 1068 |
| Thickness (mil) | 1.0 | 1.3 | 1.1 | 1.3 |

The dispersions with and without iodine anti-microbial agents were applied to human skin in small patches and allowed to dry. Adhesion was very good for all samples. Qualitatively, films made from Example 6B appeared to give better adhesion to skin. The povidone-iodine split out of the dispersions as a separate phase upon standing. The iodine-sodium iodide, however, remained uniformly distributed and stable.

Example 7

Anti-microbial Test Data

The following prepolymer was prepared as follows with an NCO/OH ratio of about 2. In a reaction vessel, under nitrogen purge and with good stirring, 132 g of NMP was mixed with 40 g DMPA (67.1 equivalent wt) and heated to about 60° C. To this mixture was added 172 g PPG 1025 (490.4 equivalent wt) and 456 g ACCLAIM 3201 (1484.1 equivalent wt). Then, 332 g DEDMODUR W isocyanate (132.2 equivalent weight) was added along with 9 drops of dibutyltin dilaurate. This mixture was heated at about 80° C. for 80 minutes. The temperature was reduced to 72° C. for an additional 40 minutes. The prepolymer was relatively low in viscosity.

A dispersion was prepared by adding 45.3 ml of IN NaOH with 212.1 g of 85:15 (wt/wt) ethanol-water mixture followed by 172.2 g of warm (60° C.) prepolymer under high shear mixing. About 5.8 g EDA was added slowly, i.e., dropwise. To the ethanol-water dispersions, varying amounts of PVP-iodine USP was added at: 0, 5, 8, and 11 wt % to yield samples 7A, 7B, 7C, and 7D.

The procedure described above was repeated replacing ethanol with IPA, to yield IPA-water dispersions. To the IPA-water dispersion, varying amounts of PVP-iodine USP was at: 0. 5. 8, and 11 wt % to yield samples 7E, 7F, 7G, and 7H. Samples 7A to 7H were tested in accordance with the MBC test, and the results are reported in the following table in units of micrograms per milliliter ($\mu$g/ml).

TABLE 18

| Example | Dispersion Type | Anti-microbial agent added | E. coli MBC ($\mu$g/ml) | S. aureus MBC ($\mu$g/ml) |
|---|---|---|---|---|
| 7A | EtOH:H$_2$O | 0% (placebo) | >16 | >16 |
| 7B | EtOH:H$_2$O | 5% PVP-iodine | 4 | 2 |
| Control for 7B | EtOH:H$_2$O | None | 1 | 0.5 |
| 7C | EtOH:H$_2$O | 8% PVP-iodine | 2 | 2 |
| Control for 7C | EtOH:H$_2$O | None | 0.5 | 0.5 |
| 7D | EtOH:H$_2$O | 11% PVP-iodine | 2 | 2 |
| Control for 7D | EtOH:H$_2$O | 11% PVP-iodine | 0.5 | 0.5 |
| 7E | IPA:H$_2$O | 0% (placebo) | >16 | >16 |
| 7F | IPA:H$_2$O | 5% PVP-iodine | 8 | 2 |
| Control for 7F | IPA:H$_2$O | 5% PVP-iodine | 2 | 0.5 |
| 7G | IPA:H$_2$O | 8% PVP-iodine | 16 | 1 |
| Control for 7G | IPA:H$_2$O | 8% PVP-iodine | 8 | 0.5 |
| 7H | IPA:H$_2$O | 11% PVP-iodine | 8 | 0.5 |
| Control for 7H | IPA:H$_2$O | 11% PVP-iodine | 8 | 0.5 |

In the table above, the Control samples contained the anti-microbial agent in the relevant alcohol-water solution. That is, the Control samples contained no polyurethane dispersion. The "placebo" sample contained the dispersion with no anti-microbial agent.

Compared to the placebo sample, which contained polyurethane dispersion but no anti-microbial agents, Examples 7B, 7C, 7D, 7F, 7G, and 7H exhibited improved anti-microbial activity. The examples containing ethanol-water polyurethane dispersion may show better activity E. coli MBC test than the IPA-water samples.

Example 8

A Higmod sulfonate polyol was made as follows. A reactor equipped with a mechanical stirrer, nitrogen purge, and distillation apparatus was charged with dimethyl-5-sodiosulfoisophthalate (700 grams, 4.73 equivalents, from Du Pont, Wilmington, Del., USA), 400 molecular weight polyethylene glycol (1947 grams, 9.735 equivalents, from, Union Carbide Corp.; Danbury, Conn., USA), and 425 molecular weight polypropylene glycol (1947 grams, 9.184 equivalents, from Arco Chemical Co.; Newton Square, Pa., USA). The reactor was heated to 345° F. (174° C.) and vacuum was applied on the reactor and held for about 1.5 hours. The vacuum was broken with nitrogen. Titanium butoxide (3.6 grams) was added and the mixture was heated to 430° F. (220° C.) and held for 3 hours while collecting methanol. The temperature was then reduced to 345° F. (174° C.) and vacuum was applied to the reaction mixture for one hour. The contents were subsequently cooled to 200° F. (93° C.) under nitrogen and drained to yield a clear, colorless liquid polyol. The measured OH equivalent weight of this polyol is 313 g/mole OH (theoretical OH of 305). The theoretical sulfonate equivalent weight of the polyol mixture is 1879 g polymer/mole sulfonate.

A prepolymer was prepared as follows: Into a one-liter heated, nitrogen purged, reaction flask equipped with an overhead air stirrer was charged the following components: (i) 75 g KRATON L-2203 hydrogenated polybutadiene diol (OH equivalent wt 1660); (ii) 250.5 g PRIPLAST 3192 polyester polyol (1058.5 equivalent wt); (iii) 64.2 g of Highmod sulfonated diol (OH equivalent wt 313) made above; and (iv) 110.3 g DESMODUR I (111.2 equivalent wt). The reaction was allowed to proceed at 80° C. for 2 hours, followed by 1 hour at 75° C. The resulting mixture was the isocyanate terminated prepolymer. The prepolymer had a NCO/OH ratio of about 2 and an NCO equivalent wt of 1008.

Three IPA-water dispersions were made using the above described prepolymer. The dispersion process is according to the general procedure of Example 1, except that a high shear Laboratory Dispersator Series 2000 Model 89 (available from Premier Mill Corporation, Reading Pa.) was used to prepare the dispersions.

TABLE 19

| Example→ | 8A | 8B | 8C |
|---|---|---|---|
| IPA:H$_2$O ratio | 70:30 | 70:30 | 83:17 |
| Percent solids | 40 | 40 | 40 |
| Prepolymer (g) | 280 | 60 | 200 |
| IPA (g) | 294 | 63 | 249 |
| Water (g) | 126 | 27 | 51 |
| EDA (g) | 7.51 | 1.61 | 6.02 |
| RESULTS: | | | |
| Viscosity (cps) | 6330 | 13250 | 48000 |
| Tensile (lb) | 3.3 | 1.8 | 5.6 |
| Tensile strength (lb/in width) | 2.75 | 1.6 | 6.2 |
| Elongation (%) | 585 | 430 | 596 |
| Thickness (mil) | 1.2 | 1.1 | 1.1 |

The results indicate that very high tensile strength films can be produced without the use of any coalescing solvent, such as NMP. The results may also indicate the higher shear mixing of the Dispersator may be beneficial.

Example 9

A prepolymer similar to that of Example 1 was prepared as follows. Into a one-liter heated, nitrogen purged, reaction flask equipped with an overhead air stirrer was charged the following components: (i) 75 g KRATON L-2203 hydrogenated polybutadiene diol (OH equivalent wt 1660); (ii) 250.5 g TERATHANE (1020 equivalent wt); (iii) 64.2 g of Highmod sulfonated diol (OH equivalent wt 313); and (iv) 110.3 g DESMODUR I (111.2 equivalent wt). Dibutyltin dilaurate catalyst was added and the reaction temperature peaked at about 94° C. The reaction was allowed to proceed at 80° C. for 2 hours, followed by 1 hour at 75° C. The resulting mixture was the isocyanate terminated prepolymer. The prepolymer had a NCO/OH ratio of about 2 and a NCO equivalent weight of 1008.

Four IPA-water dispersions were made using the above described prepolymer. The dispersion process is according to the general procedure of Example 1.

TABLE 20

| Example→ | 9A | 9B | 9C | 9D |
|---|---|---|---|---|
| IPA-H$_2$O ratio | 90:10 | 85:15 | 80:20 | 75:25 |
| Percent solids | 40 | 40 | 40 | 40 |
| Prepolymer (g) | 60 | 60 | 60 | 60 |
| IPA (g) | 81 | 76.5 | 72 | 67.5 |
| Water (g) | 9 | 13.5 | 18 | 22.5 |
| EDA (g) | 2.05 | 2.05 | 2.05 | 2.05 |

TABLE 20-continued

| Example→ | 9A | 9B | 9C | 9D |
|---|---|---|---|---|
| RESULTS: | | | | |
| Viscosity (cps) | 145000 | 108000 | 621500 | 66200 |
| Tensile (lb) | 8.2 | 8.1 | 5.8 | 3.4 |
| Tensile strength (lb/in width) | 6.3 | 6.8 | 4.8 | 2.6 |
| Elongation (%) | 741 | 750 | 773 | 918 |
| Thickness (mil) | 1.3 | 1.2 | 1.2 | 1.3 |

To Example 9C was added 3.0 g of ZONYL FSN (a fluorosurfactant from DuPont). To Example 9D was added 2% by weight (3 gram) SILWAX WD-IS (a surfactant from Goldschmidt Chemical). The results indicated that very high tensile strength films can be produced without the use of a coalescing solvent such as NMP. The results may also indicate that the surfactant addition may adversely affect tensile strength. However, even with the surfactants present to help disperse the prepolymer, the tensile strengths of Examples 9C and 9D were relatively high.

Example 10

A prepolymer similar to that of Example 1 was prepared as follows. Into a one-liter heated, nitrogen purged, reaction flask equipped with an overhead air stirrer was charged the following components: (i) 177.2 g PRIPLAST 3197 polyester polyol (1122 equivalent wt ); (ii) 52.35 g PRIPOL 2033 $C_{36}$ dimer fatty alcohol (277.7 equivalent wt); (iii) 81 g of Highmod sulfonated diol (313 equivalent wt); and (iv) 138.5 g DESMODUR I (111.2 equivalent wt). The dibutylin-(1-mercaptoethanol((1-thioglycerol) catalyst, described in Example 3, was added. The reaction was allowed to proceed at 80° C. for 2 hours, followed by 1 hour at 75° C. The resulting mixture was the isocyanate terminated prepolymer. The prepolymer had a NCO/OH ratio of about 2 and a NCO equivalent weight of 722.

Six IPA-water dispersions were made using the above described prepolymer.

The dispersion process was according to the general procedure of Example 1.

TABLE 21

| Example→ | 10A | 10B | 10C | 10D | 10E | 10F |
|---|---|---|---|---|---|---|
| IPA:H$_2$O ratio | 90:10 | 85:15 | 80:20 | 75:25 | 70:30 | 65:35 |
| Percent solids | 40 | 40 | 40 | 40 | 40 | 40 |
| Prepolymer (g) | 60 | 60 | 60 | 60 | 60 | 60 |
| IPA (g) | 81 | 76.5 | 72 | 67.5 | 63 | 58.5 |
| Water (g) | 9 | 13.5 | 18 | 22.5 | 27 | 31.5 |
| EDA (g) | 2.25 | 2.25 | 2.25 | 2.25 | 2.25 | 2.25 |
| RESULTS: | | | | | | |
| Viscosity (cps) | 8550 | 9990 | 9150 | 6080 | 4995 | 5425 |
| Tensile (lb) | 3.1 | 4.2 | 2.7 | 2.4 | 2.2 | 1.7 |
| Tensile strength (lb/in width) | 3.1 | 3.8 | 2.5 | 2.4 | 2 | 1.5 |
| Elongation (%) | 271 | 344 | 325 | 388 | 419 | 374 |
| Thickness (mil) | 1.0 | 1.1 | 1.1 | 1.0 | 1.1 | 1.1 |

The results indicate that high tensile strength films can be produced without the use of a coalescing solvent, such as NMP. The results may also indicate that for this prepolymer, higher alcohol concentration result in stronger films.

Example 11

The following prepolymer was prepared under nitrogen purge with good stirring in general accordance with Example 1 except that dibutylin-(1-mercaptoethanol((1-thioglycerol) catalyst, described in Example 3, was added (1 g added to the prepolymer). The reaction temperature peaked at 100° C. after adding the catalyst. The reaction was cooled to 75° C. and allowed to continue for 3 hours. The exact formulations of prepolymers I and J are shown below:

TABLE 22

| | Equivalent wt. (g/eq) | Prepolymer I | Prepolymer J |
|---|---|---|---|
| NCO/OH | | About 2 | About 2.1 |
| NCO Equivalent wt | | 873 | 800 |
| DESMODUR I (g) | 111.2 | 127.4 | 132.6 |
| KRATON L2203 (g) | 1660 | 40 | 40 |
| Himod sulfonated diol (g) | 300 | 75 | 75 |
| Octanol (g) | 130.2 | 6 | 6 |
| TERATHANE 2000 (g) | 1020 | 250.6 | 245.4 |

The prepolymers were used to produce dispersions in IPA:water solvent systems according to the general procedure of Example 1 using the components listed in Table 23.

TABLE 23

| Example→ | 11A | 11B | 11C | 11D | 11E | 11F | 11G | 11H | 11I | 11J | 11L | 11K |
|---|---|---|---|---|---|---|---|---|---|---|---|---|
| IPA:H$_2$O ratio | 90/10 | 85/15 | 80/10 | 75/25 | 70/30 | 65/35 | 90/10 | 85/15 | 80/10 | 75/25 | 70/30 | 65/35 |
| Percent solids | 40 | 40 | 40 | 40 | 40 | 40 | 40 | 40 | 40 | 40 | 40 | 40 |
| Prepolymer I (g) | 60 | 60 | 60 | 60 | 60 | 60 | 0 | 0 | 0 | 0 | 0 | 0 |
| Prepolymer J (g) | 0 | 0 | 0 | 0 | 0 | 0 | 60 | 60 | 60 | 60 | 60 | 60 |
| IPA (g) | 81 | 76.5 | 72 | 67.5 | 63 | 58.5 | 81 | 76.5 | 72 | 67.5 | 63 | 58.5 |
| Water (g) | 9 | 13.5 | 18 | 22.5 | 27 | 31.5 | 9 | 13.5 | 18 | 22.5 | 27 | 31.5 |
| EDA (g) | 1.86 | 1.86 | 1.86 | 1.86 | 1.86 | 1.86 | 2.03 | 2.03 | 2.03 | 2.03 | 2.03 | 2.03 |
| RESULTS: | | | | | | | | | | | | |
| Viscosity (cps) | 6155 | 11875 | 14375 | 14640 | 18040 | 24225 | 6325 | 11245 | 10080 | 11085 | 22800 | 34500 |
| Tensile (lb) | 2 | 3.8 | 3.9 | 3.2 | 3 | 3.2 | 3.1 | 4.4 | 3.9 | 3.1 | 4.8 | 6 |
| Tensile strength (lb/in width) | 2 | 3.8 | 3.9 | 2.91 | 2.73 | 2.67 | 2.82 | 4.4 | 3.9 | 3.1 | 4.36 | 5 |
| Elongation (%) | 998 | 872 | 889 | 902 | 881 | 850 | 853 | 778 | 835 | 848 | 707 | 722 |
| Thickness (mil) | 1.0 | 1.0 | 1.0 | 1.1 | 1.1 | 1.2 | 1.1 | 1.0 | 1.0 | 1.0 | 1.1 | 1.2 |

The results show that, in general, the viscosity of the dispersions were very low. The dispersion viscosity did increase, however, with decreasing IPA-water ratio. The tensile strength of prepolymer J, which had a higher NCO/OH ratio and a lower NCO equivalent wt, was generally higher. The elongation of films made from prepolymer J dispersions was less than the corresponding dispersions of prepolymer I. These examples show that a relatively low level of mono-functional alcohol may be beneficial in producing low viscosity dispersions with high tensile strength.

Example 12

The dispersions of Example 9B we knife coated onto a polypropylene coated paper release liner and sprayed with water solutions containing the following materials. The film appearance was recorded in the Result column.

TABLE 24

| Compound | Result |
| --- | --- |
| Sodium Chloride (10 wt %) | Random coagulation. Appears similar to cottage cheese |
| Calcium chloride (7.5 wt %) | Almost instantaneous tack-free film. Solvent appears to exude out of film |
| Calcium Citrate (7.5 wt %) | No effect |
| Celquat SC240- quaternary cellulose derivative (7.5 wt %) | Random coagulation. Appears similar to cottage cheese |

This examples shows that certain polyvalent cations including metal cations such as calcium may be used to yield almost instantaneously tack free films.

Example 13

Use of Tri-functional Chain Extenders

A prepolymer similar to that of Example 1 was prepared as follows. Into a one-liter heated, nitrogen purged, reaction flask equipped with an overhead air stirrer was charged the following components: (i) 76.5 g KRATON L2203 (1660 equivalent wt); (ii) 300 g PRIPLAST 3192 polyester polyol (1039 equivalent wt); (iii) 84 g of Highmod sulfonated diol (OH equivalent wt 313); and (iv) 138 g DESMODUR I (111.2 equivalent wt). The dibutylin-(1-mercaptoethanol((1-thioglycerol) catalyst, described in Example 3 was added. The reaction was allowed to proceed at 80° C. for 2 hours, followed by 1 hours at 75° C. The resulting mixture was the isocyanate terminated prepolymer. The prepolymer had a NCO/OH ratio of about 1.99 and a NCO equivalent weight of 1061.

Three IPA-water dispersions were made using the above described prepolymer. The dispersion process was according to the general procedure of Example 1 using the components listed below. The trifunctional chain extender, TREN (trisaminoethylamine), was added to the IPA-water solvent system prior adding the prepolymer. The total amine equivalent was fixed at 90% of the theoretical NCO equivalents.

TABLE 25

| Example→ | 13A | 13B | 13C |
| --- | --- | --- | --- |
| IPA-H$_2$O Ratio | 70/30 | 70/30 | 70/30 |
| Percent solids | 40 | 40 | 40 |
| Prepolymer (g) | 60 | 60 | 60 |
| IPA (g) | 63 | 63 | 63 |

TABLE 25-continued

| Example→ | 13A | 13B | 13C |
| --- | --- | --- | --- |
| Water (g) | 27 | 27 | 27 |
| TREN (g) | 0.27 | 0.53 | 0.8 |
| EDA (g) | 1.53 | 1.61 | 1.62 |
| TREN/EDA eq. ratio | 10/90 | 20/80 | 30/70 |
| RESULTS: | | | |
| Viscosity (cps) | 2045 | 2360 | Gelled |
| Tensile (lb) | 3 | 3.1 | NA |
| Tensile strength (lb/in width) | 3.0 | 2.8 | NA |
| Elongation (%) | 556 | 561 | NA |
| Thickness (mil) | 1.0 | 1.1 | NA |

The results showed that when 30% of the amine equivalents were trifunctional TREN, the crosslink density was sufficiently high to cause the dispersion to gel. Below this level, however, low viscosity dispersions with good tensile and elongation properties resulted. "NA" means not available.

Example 14

Rapid Dry Film-Forming Compositions using Lower Heat of Vaporization Solvent

As discussed, the use of some alcohol-water solvent system may be desirable in anti-microbial formulations to achieve rapid microbial kill, e.g., the alcohol (ethanol or IPA) to water ratio should be 60 to 90% by weight alcohol. In order to obtain a rapid drying film, higher alcohol levels are desirable (because the lower alcohols have a lower heat of vaporization compared to water In order to achieve faster dry times two main approaches were evaluated. The first approach focused on replacing a portion of the alcohol-water solvent with a lower heat of vaporization solvent. The second approached focused on replacing a portion of the alcohol-water solvent in the dispersion with a plasticizer that will remain in the film.

It has been found that to maintain high percent solids in the dispersions, the concentration of alcohol-water insoluble components (the "A" component) in the prepolymer should be maintained at relatively high levels. As stated, lowering the percent solids in the dispersion would prolong dry time of the dispersion, an undesirable feature.

As the concentration of the lower heat of vaporization solvent is increased, the relative concentration of prepolymer components should be altered and/or the components themselves should be altered. Suitable low heat of vaporization solvents include HMDS (hexamethyldisiloxane) and volatile isoparafins, such as ISOPAR C (available from Exxon Company). These solvents have a solubility limit in the alcohol-water system. Preferably the solubility limit is not exceeded.

The following prepolymers were prepared under nitrogen purge with good stirring in general accordance with Example 1 except that the catalyst was Fastcat 4224 About 1 g of the catalyst was added to the prepolymer. The exact formulations of prepolymers K and L are shown below.

TABLE 26

| | Equivalent wt (g/equiv) | Prepolymer K | Prepolymer L |
| --- | --- | --- | --- |
| NCO/OH ratio | | 2.1 | 2 |
| NCO equivalent wt | | 864 | 898 |
| DESMODUR I (g) | 111 | 147.33 | 148.6 |

TABLE 26-continued

| | Equivalent wt (g/equiv) | Prepolymer K | Prepolymer L |
|---|---|---|---|
| KRATON L2203 (g) | 1660 | 0 | 120 |
| Himod sulfonated diol (g) | 300 | 84 | 75 |
| TERATHANE 2000 (g) | 1020 | 0 | 244.5 |
| SURFYNOL 104 (g) | 113 | 0 | 12 |
| PRIPLAST 1907 (g) | 1020 | 84 | 0 |
| PRIPLAST 3192 (g) | 1059 | 284.6 | 0 |

The two prepolymers were used to make dispersions in IPA-water-HMDS or IPA-water-ISOPARC generally in accordance with the procedure of Example 1, except that the indicated amount of HMDS or ISOPAR C (shown in Table 27) was added to the IPA-water prior to adding the prepolymer. To make the dispersions, 50 g of prepolymer was dispersed in a total solvent amount of 75 g. EDA was added to chain extend the prepolymer. It was added at about 95% of the theoretical equivalent of isocyanate in the prepolymer (i.e., for 50 g of prepolymer A, 1.65 g of EDA was used; for 50 g of prepolymer B, 1.60 g of EDA was used). Examples 14A to 14 F were made from prepolymer K. Examples 14G to 14L were made from prepolymer L.

TABLE 27

| Example | Amount of 85:15 IPA-H$_2$O (g) | Solvent type | Solvent amount (g) | Dry Time (sec) |
|---|---|---|---|---|
| Prepolymer A | | | | |
| 14A | 65 | HMDS | 10 | <90 |
| 14B | 55 | HMDS | 20 | <90 |
| 14C | 50 | HMDS | 25 | ND |
| 14D | 65 | ISOPAR C | 10 | <15 |
| 14E | 55 | ISOPAR C | 20 | ND |
| 14F | 50 | ISOPAR C | 25 | ND |
| Prepolymer B | | | | |
| 14G | 65 | HMDS | 10 | <90 |
| 14H | 55 | HMDS | 20 | <60 |
| 14I | 50 | HMDS | 25 | <60 |
| 14J | 65 | ISOPAR C | 10 | <90 |
| 14K | 55 | ISOPAR C | 20 | <90 |
| 14L | 50 | ISOPAR C | 25 | ND |

ND means not determined. Example 14C was a white, semi-waxy gel that could not be dispersed. Similarly, Examples 14E, 14F, and 14L were semi-clear, clear, and translucent gels respectively, and thus could not be mixed uniformly. In the table above, dry time was determined qualitatively by coating a 0.008 inch (0.20 mm) wet thickness film of the dispersion onto a release liner and allowing it to air dry under ambient conditions. Furthermore when water was sprayed over the surface of the dried dispersion, the film skinned over almost immediately (i.e., in less than about 15 seconds).

Example 15

Rapid Dry Film-Forming Compositions using Plasticizers

In this example, various plasticizers were added to the solvent system to reduce the total volatile content. To maintain tough films with good physical properties, the prepolymer formulation was adjusted. The NCO/OH ratio was increased and the NCO equivalent weight was decreased.

A prepolymer similar to that of Example 1 was prepared as follows. Into a one-liter heated, nitrogen purged, reaction flask equipped with an overhead air stirrer was charged the following components: (i) 119.7 g KRATON L2203 (1660 equivalent wt); (ii) 227.3 g TERATHANE 2000 (1020 equivalent wt); (iii) 75 g of Highmod sulfonated diol (OH equivalent wt 313); (iv) 166.3 g DESMODUR I (111.2 equivalent wt); and (v) 12 g SURFYNOL 104 (113 equivalent wt). About 1 g Fastcat 4224catalyst, was added. The reaction was allowed to proceed at 80° C. for 2 hours, followed by 1 hours at 75° C. The resulting mixture was the isocyanate terminated prepolymer. The prepolymer had a NCO/OH ratio of about 2.3 and a NCO equivalent weight of 710.

The prepolymer was used to make dispersions in 85:15 IPA-water. The total amount of solvent and plasticizer was fixed at 75 g to be used with 50 g of prepolymer. Also, 2.01 g of EDA was used as a chain extender for each dispersion. The following dispersions were prepared as shown below.

TABLE 28

| Example | Plasticizer Type | 85.15 IPA/water (g) | Plasticizer (g) | Results |
|---|---|---|---|---|
| 15A | None | 75 | 0 | Good dispersion but thick |
| 15B | DIPS | 60 | 15 | Thick dispersion |
| 15C | DIPS | 50 | 25 | Thick dispersion |
| 15D | Triacetin | 60 | 15 | Thick dispersion |
| 15E | GTCC | 60 | 15 | Thick dispersion |

DIPS means diisopropylsebacate, Dermol DIPS available Alzo Inc., Sayerville, N.J. GTCC means glyceroltricaprylat/caprate, Crodamol GTCC, available from Croda Inc. NY, N.Y.

The dispersions of Examples 15A to 15E were very thick. For this reason, they were repeated with 70:30 IPA-water (w/w) in place of the 85:15. The 70:30 IPA-water dispersions were much less viscous and can be coated easily. The 70:30 dispersions were coated onto release liner as done in Example 14 and found to have dry times of about 60 to 85 seconds. If misted with water, the tack free times were less than 30 seconds.

Example 16

A dispersion like that of Example 15A was produced by dispersing 220 g of prepolymer into 330 g 85:15 IPA-water solvent mixture along with 6.9 g of EDA (93.7% of theoretical). The dispersion and polyurethane films therefrom were made generally in accordance with Example 1. A 0.001 inch polyurethane film had a tensile strength of 5.9 lb/in width and 710% elongation. To this dispersion was added 7.5% by weight povidone-iodine USP.

To a portion of the dispersion was added a very volatile solvent—methyl acetate (at about 10% by weight) to reduce viscosity. The dispersion was applied to the cleaned belly of a pig. Both dispersions, i.e., one with methyl acetate and one without, were applied with a bristle paintbrush. Due to the dispersion viscosity, streaks were left in the dried incise film. The dispersions dried to adherent films. The dispersion containing methyl acetate appeared to dry faster. The films were incised through. They remained adhered to the pig skin during the surgical procedure. After surgery, the films could be removed in large pieces.

Example 17

The following prepolymers were prepared under nitrogen purge with good stirring in general accordance with Example 1. The reaction temperature was maintained at about 80° C. for 2.5 hours. The exact formulations of prepolymers M and N are shown below.

TABLE 29

| | Equivalent wt (g/equiv) | Prepolymer M | Prepolymer N |
|---|---|---|---|
| NCO/OH ratio | | 2 | 2 |
| NCO equivalent wt | | 1098 | 1151 |
| DESMODUR I (g) | 111 | 127.8 | 115.9 |
| KRATON L2203 (g) | 1660 | 156.6 | 150.7 |
| TERATHANE 2000 (g) | 1020 | 315.1 | 303.4 |
| SURFYNOL 104 (g) | 113 | 6.31 | 6.00 |
| Sulfopolyester diol of Example 1 | 218 | 25.2 | 24 |

These prepolymers were used to produce dispersions in EPA-water solvent systems according to the general procedure of Example 1 using the components listed in the following table.

TABLE 30

| Example→ | 17A | 17B | 17C | 17D | 17E | 17F | 17G | 17H | 17I | 17J | 17K | 17L |
|---|---|---|---|---|---|---|---|---|---|---|---|---|
| IPA-H$_2$O ratio | 90/10 | 85/15 | 80/20 | 75/25 | 70/30 | 65/35 | 90/10 | 85/15 | 80/20 | 75/25 | 70/30 | 65/35 |
| Percent solids | 40 | 40 | 40 | 40 | 40 | 40 | 40 | 40 | 40 | 40 | 40 | 40 |
| Prepolymer A (g) | 60 | 60 | 60 | 60 | 60 | 60 | 0 | 0 | 0 | 0 | 0 | 0 |
| Prepolymer B (g) | 0 | 0 | 0 | 0 | 0 | 0 | 60 | 60 | 60 | 60 | 60 | 60 |
| IPA (g) | 81 | 76.5 | 72 | 67.5 | 63 | 58.5 | 81 | 76.5 | 72 | 67.5 | 63 | 58.5 |
| Water (g) | 9 | 13.5 | 18 | 22.5 | 27 | 31.5 | 9 | 13.5 | 18 | 22.5 | 27 | 31.5 |
| EDA (g) | 1.48 | 1.48 | 1.48 | 1.48 | 1.48 | 1.48 | 1.41 | 1.41 | 1.41 | 1.41 | 1.41 | 1.41 |
| Self Stick | good | good | poor | none | none | none | Very good | good | weak | weak | NA | NA |

The composition of Examples 17A, 17B, 17G, and 17H showed self adhesion properties. Thus, such compositions can be coated onto the back-side of a film product and can be adhered to a dried film of these samples on a second substrate. For example, if an incise drape or apertured surgical drape were coated on the underside with these compositions the drapes could be easily adhered to a dried prep of one of these samples. This would simplify the draping process in surgery.

All references cited herein are incorporated by reference, in each reference's entirety.

What is claimed is:

1. A polyurethane dispersion, said polyurethane comprising the reaction product of:
    (a) an isocyanate functional prepolymer comprising the reaction product of (i) at least one polyactive hydrogen compound, wherein said compound is an alkyl, aryl, or aralkyl structure optionally substituted in or on the chain or both in and on the chain by N, O or S, or combinations thereof, and wherein said compound is insoluble in a lower alcohol-water mixture having an alcohol to water ratio of at least 50:50 by weight; (ii) at least one polyisocyanate, and (iii) at least one active hydrogen compound soluble in said lower alcohol-water mixture selected from the group consisting of a compound containing an ionic group, a compound containing a moiety capable of forming an ionic group, a compound containing a polyester, polyether, or polycarbonate group having a ratio of 5 or less carbon atoms for each oxygen atom and mixtures thereof; and
    (b) at least one polyfunctional chain extender; wherein the dispersion has a continuous phase comprising a lower alcohol-water mixture having at least twenty weight percent alcohol.

2. The polyurethane dispersion of claim 1, wherein the equivalent ratio of said chain extender to isocyanate functional prepolymer is 0.60:1 to 1.20:1.

3. The dispersion of claim 1, wherein said lower alcohol in the alcohol-water mixture is selected from the group consisting of ethanol, 2-propanol, and n-propanol.

4. The dispersion of claim 2, wherein said lower alcohol-water mixture has a lower alcohol to water ratio of at least 60:40 by weight.

5. The dispersion of claim 1, wherein component (a)(i) is selected from the group consisting of oligomeric polyactive hydrogen compounds having on average from about 1.6 to 4 hydroxyl and/or amino groups.

6. The dispersion of claim 1, wherein component (a)(i) is selected from the group consisting of active hydrogen functional polybutadiene, polyisoprene, hydrogenated polybutadiene, hydrogenated polyisoprene, and combinations thereof.

7. The dispersion of claim 1 comprising at least 10 percent by weight of component (a)(i) based on the total weight of components a(i), a(ii), and a(iii).

8. The dispersion of claim 1, wherein said polyisocyanate is selected from the group consisting of dicyclohexylmethane 4,4'-diisocyanate; 3,5,5-trimethyl-1-isocyanato-3-isocyanatomethylcyclohexane; tetramethylene diisocyanate; 1,3-bis(isocyanatomethyl)cyclohexane; 1,3-bis(1-isocyanato-1-methylethyl)benzene; diphenylmethane 4,4'-diisocyanate; 4,4', 4"-triisocyanatotriphenylmethane; polymethylene polyphenylene polyisocyanate; toluene diisocyanate; hexamethylene diisocyanate; dodecamethylene diisocyanate; m- and p-xylene diisocyanate and combinations thereof.

9. The dispersion of claim 1, wherein component (a)(iii) is a cationic compound having the following structure:

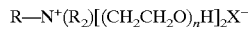

wherein

R is $C_1$ to $C_{18}$ alkyl or $C_6$ to $C_{18}$ aryl or aralkyl optionally substituted in or on the chain by N, O, or S;

$R_2$ is hydrogen or $C_1$ to $C_{18}$ alkyl;

n is an integer from 1 to 200; and

X is a halogen, sulfate, methosulfate, ethosulfate, acetate, carbonate, or phosphate.

10. The dispersion of claim 1, wherein component (a)(iii) is a compound having the following structure:

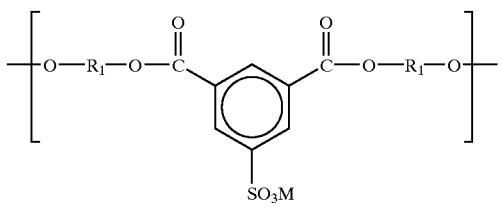

wherein each $R_1$ is independently a divalent aliphatic group having an average molecular weight of 200 to 2000 comprising ether or ester functional groups selected from the group consisting of —$CH_2$—$CH_2$—($OCH_2$—$CH_2$—)$_n$—, —($CH_2$)$_4$—($O(CH_2)_4$)$_n$—, —$C(CH_3)H$—$CH_2$—($OC(CH_3)H$—$CH_2$—)$_n$—, and —($CH_2$)$_m$—CO—[—O—($CH_2$)$_m$—CO—]$_n$—groups;

where m is an integer from 2 to 5 and n is an integer from 2 to 15; and M is selected from the group consisting of Na, H, K, Li, ammonium, methylammonium, butylammonium, diethylammonium, triethylammonium, tetraethylammonium and benzyltrimethyl-ammonium cation.

11. The dispersion of claim 1, wherein said chain extender is selected from the group consisting of water; aliphatic diamines; piperazine; tris(2-aminoethyl)amine; amine terminated polyethers; adipic acid dihydrazide; oxalic acid dihydrazides; ethylene glycol; 1,4 butane diol; 1,8 octane diol; 1,2-ethanedithiol; 1,4-butanedithiol; 2,2'-oxytris (ethane thiol); and di- and tri-mercaptopropionate esters of poly(oxyethylene) diols and triols.

12. The dispersion of claim 11 wherein said chain extender is ethylene diamine.

13. The dispersion of claim 1 further comprising a solvent having a heat of vaporization of no more than 125 calories per gram.

14. The dispersion of claim 13 wherein said solvent is selected from the group consisting of hexamethyldisiloxane, octane, hexane, and combinations thereof.

15. The dispersion of claim 1 further comprising an anti-microbial agent selected from the group consisting of iodine-sodium iodide, iodine-potassium iodide, povidone-iodine complex, chlorhexidine gluconate, and combinations thereof.

16. A liquid drape, a pre-surgical patient prep, or a combination thereof comprising the dispersion of claim 15.

17. The dispersion of claim 1, wherein said aqueous ionic polyurethane dispersion has an ionic content of about 1,000 to 15,000 gram of prepolymer per equivalent of ionic group.

18. The dispersion of claim 1, wherein said reaction product has a weight average molecular weight of about 5,000 to 50,000.

19. The dispersion of claim 1 exhibiting self-adhesion properties when coated and dried to a film of about 0.25 millimeter in thickness.

20. The dispersion of claim 1 having a dry time of less than 5 minutes.

21. The dispersion of claim 1 further comprising an additive selected from the group consisting of plasticizers, defoaming agents, flow and leveling agents, rheology modifiers, photostabilizers, and combinations thereof.

22. The dispersion of claim 21, wherein said plasticizer is an emollient.

23. The dispersion of claim 21 wherein said plasticizer is selected from the group consisting of diisopropylsebacate, triacetin, glyceroltricaprylate-caprate, and combinations thereof.

24. The dispersion of claim 1 further comprising a solvent selected from the group consisting of methyl ethyl ketone, methoxypropanol acetate, dimethyl acetamide, tetrahydrofuran, N-methyl-pyrrolidinone, and combinations thereof.

25. The dispersion of claim 1, wherein component (a)(iii) is a poly($C_2$ to $C_4$ alkylene oxide).

26. A kit comprising a drape and a receptacle containing the dispersion of claim 1.

27. The kit of claim 26, wherein said drape further comprises a film attached to at least a portion of said drape, said film formed from the dispersion of claim 1.

28. A method of using the kit of claim 26 comprising the steps of:

(a) applying said dispersion from said receptacle to a patient's skin to form a self-adherent incise drape, (b) applying said drape such that said film is in direct contact with the patient's skin.

29. A method of making a polyurethane dispersion that is stable in a lower alcohol-water mixture containing at least about twenty percent by weight alcohol, said method comprising the steps of:

(a) providing at least one isocyanate functional prepolymer comprising the reaction product of (i) at least one oligomeric polyactive hydrogen compound, wherein said compound is an alkyl, aryl, or aralkyl structure optionally substituted in and/or on the chain by N, O, and S, and wherein said compound is insoloble in said alcohol-water mixture, when the alcohol to water ratio is at least 50:50 by weight; (ii) at least one polyisocyanate, and (iii) at least one active hydrogen compound soluble in said alcohol-water mixture selected from the group consisting of a compound containing an ionic group, a compound containing a moiety capable of forming an ionic group, a compound containing a polyester, polyether, or polycarbonate group having a ratio of 5 or less carbon atoms for each oxygen atom and mixtures thereof; and (b) dispersing said prepolymer in said alcohol-water mixture; and then (c) adding at least one polyfunctional chain extender.

* * * * *

UNITED STATES PATENT AND TRADEMARK OFFICE
CERTIFICATE OF CORRECTION

| | |
|---|---|
| PATENT NO. | : 6,605,666 B1 |
| APPLICATION NO. | : 09/627110 |
| DATED | : August 12, 2003 |
| INVENTOR(S) | : Matthew T. Scholz et al. |

It is certified that error appears in the above-identified patent and that said Letters Patent is hereby corrected as shown below:

Column 6
Line 44, delete "$C_{,18}$" and insert in place thereof -- $C_{18}$ --.
Line 64, delete "perflouroalkyl" and insert place thereof -- perfluoroalkly --.

Column 8
Line 46, delete "$R-N^{30}(R_2[(CH_2CH_2O)_nH]_2X^-$" and insert in place thereof
 -- $R-N^+(R_2[(CH_2CH_2O)_nH]_2X^-$ --.
Line 63, delete "inlcude" and insert in place thereof -- include --.

Column 13
Line 18, delete "consisting," and insert in place thereof -- consisting --.

Column 16
Line 16, after "formulated" insert -- to --.
Line 18, after "use" insert -- of --.

Column 20
Line 5, delete "dispersions" and insert in place thereof -- dispersion --.
Line 8, after "levels" insert -- of --.

Column 22
Line 12, delete "70.20" and insert in place thereof -- 70.30 --.

Column 24
Line 5, delete "call" and insert in place thereof -- all --.

Column 29
Line 36, after "activity" insert -- for --.

UNITED STATES PATENT AND TRADEMARK OFFICE
CERTIFICATE OF CORRECTION

PATENT NO. : 6,605,666 B1
APPLICATION NO. : 09/627110
DATED : August 12, 2003
INVENTOR(S) : Matthew T. Scholz et al.

It is certified that error appears in the above-identified patent and that said Letters Patent is hereby corrected as shown below:

Column 30
Lines 17-31, delete "Table 19" and insert the following table in place thereof.

TABLE 19

| Example→ | 8A | 8B | 8C |
|---|---|---|---|
| IPA:H$_2$O ratio | 70:30 | 70:30 | 83:17 |
| Percent solids | 40 | 40 | 40 |
| Prepolymer (g) | 280 | 60 | 200 |
| IPA (g) | 294 | 63 | 249 |
| Water (g) | 126 | 27 | 51 |
| EDA (g) | 7.51 | 1.61 | 6.02 |
| RESULTS: | | | |
| Viscosity (cps) | 6330 | 13250 | 48000 |
| Tensile (lb) | 3.3 | 1.8 | 5.6 |
| Tensile strength (lb/in width) | 2.75 | 1.6 | 6.2 |
| Elongation (%) | 585 | 430 | 596 |
| Thickness (mil) | 1.2 | 1.1 | 1.1 |

Column 40
Line 44, delete "and" and insert in place thereof -- or --.
Line 44, delete "insoloble" and insert in place thereof -- insoluble --.

Signed and Sealed this

Twenty-fourth Day of October, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,605,666 B1 | |
| APPLICATION NO. | : 09/627110 | |
| DATED | : August 12, 2003 | |
| INVENTOR(S) | : Matthew T. Scholz et al. | |

It is certified that error appears in the above-identified patent and that said Letters Patent is hereby corrected as shown below:

Column 6
Line 44, delete "$C_{,18}$" and insert in place thereof -- $C_{18}$ --.
Line 64, delete "perflouroalkyl" and insert place thereof -- perfluoro alkyl --.

Column 8
Line 46, delete "$R-N^{30}(R_2[(CH_2CH_2O)_nH]_2X^-$" and insert in place thereof
-- $R-N^+(R_2[(CH_2CH_2O)_nH]_2X^-$ --.
Line 63, delete "inlcude" and insert in place thereof -- include --.

Column 13
Line 18, delete "consisting," and insert in place thereof -- consisting --.

Column 16
Line 16, after "formulated" insert -- to --.
Line 18, after "use" insert -- of --.

Column 20
Line 5, delete "dispersions" and insert in place thereof -- dispersion --.
Line 8, after "levels" insert -- of --.

Column 22
Line 12, delete "70.20" and insert in place thereof -- 70.30 --.

Column 24
Line 5, delete "call" and insert in place thereof -- all --.

Column 29
Line 36, after "activity" insert -- for --.

UNITED STATES PATENT AND TRADEMARK OFFICE
CERTIFICATE OF CORRECTION

PATENT NO. : 6,605,666 B1
APPLICATION NO. : 09/627110
DATED : August 12, 2003
INVENTOR(S) : Matthew T. Scholz et al.

It is certified that error appears in the above-identified patent and that said Letters Patent is hereby corrected as shown below:

Column 30
Lines 17-31, delete "Table 19" and insert the following table in place thereof.

TABLE 19

| Example→ | 8A | 8B | 8C |
|---|---|---|---|
| IPA:H$_2$O ratio | 70:30 | 70:30 | 83:17 |
| Percent solids | 40 | 40 | 40 |
| Prepolymer (g) | 280 | 60 | 200 |
| IPA (g) | 294 | 63 | 249 |
| Water (g) | 126 | 27 | 51 |
| EDA (g) | 7.51 | 1.61 | 6.02 |
| RESULTS: | | | |
| Viscosity (cps) | 6330 | 13250 | 48000 |
| Tensile (lb) | 3.3 | 1.8 | 5.6 |
| Tensile strength (lb/in width) | 2.75 | 1.6 | 6.2 |
| Elongation (%) | 585 | 430 | 596 |
| Thickness (mil) | 1.2 | 1.1 | 1.1 |

Column 40
Line 44, delete "and" and insert in place thereof -- or --.
Line 44, delete "insoloble" and insert in place thereof -- insoluble --.

This certificate supersedes Certificate of Correction issued October 24, 2006.

Signed and Sealed this

Fifth Day of June, 2007

JON W. DUDAS
*Director of the United States Patent and Trademark Office*